(12) United States Patent
Khan et al.

(10) Patent No.: US 11,672,830 B2
(45) Date of Patent: Jun. 13, 2023

(54) MICRORNA-294 AND LIN28A AS A DRIVER OF CARDIAC TISSUE PROLIFERATION IN RESPONSE TO PATHOLOGICAL INJURY

(71) Applicant: Temple University—Of The Commonwealth System of Higher Education, Philadelphia, PA (US)

(72) Inventors: Mohsin Khan, Sewell, NJ (US); Raj Kishore, Devon, PA (US)

(73) Assignee: Temple University-Of The Commonwealth System of Higher Education, Philadelphia, PA (US)

( * ) Notice: Subject to any disclaimer, the term of this patent is extended or adjusted under 35 U.S.C. 154(b) by 597 days.

(21) Appl. No.: 16/093,689

(22) PCT Filed: Apr. 17, 2017

(86) PCT No.: PCT/US2017/027876
§ 371 (c)(1),
(2) Date: Oct. 15, 2018

(87) PCT Pub. No.: WO2017/181166
PCT Pub. Date: Oct. 19, 2017

(65) Prior Publication Data
US 2020/0323924 A1    Oct. 15, 2020

Related U.S. Application Data

(60) Provisional application No. 62/323,002, filed on Apr. 15, 2016.

(51) Int. Cl.
*A61K 35/34* (2015.01)
*C12N 5/077* (2010.01)
*C12N 15/113* (2010.01)

(52) U.S. Cl.
CPC ............. *A61K 35/34* (2013.01); *C12N 5/0657* (2013.01); *C12N 15/113* (2013.01); *C12N 2310/141* (2013.01); *C12N 2501/65* (2013.01)

(58) Field of Classification Search
CPC .................................................... A61K 35/34
See application file for complete search history.

(56) References Cited

U.S. PATENT DOCUMENTS

| | | | |
|---|---|---|---|
| 2012/0128655 A1 | 5/2012 | Kim | |
| 2013/0195899 A1 | 8/2013 | Ichim | |
| 2013/0244262 A1 | 9/2013 | Yamashita | |
| 2015/0133531 A1* | 5/2015 | Wiegand | ................. A61P 37/06 514/44 R |

FOREIGN PATENT DOCUMENTS

| WO | 2009105044 | 8/2009 |
|---|---|---|
| WO | 2015004539 A2 | 1/2015 |

OTHER PUBLICATIONS

Cyganek et al. (J Clin Exp Cardiolog 2013, S11 http://dx.doi.org/10.4172/2155-9880.S11-008). (Year: 2013).*
Khan et al. (Circulation Research 2014; 115:A129; Poster session 2, Abstract 129: Embryonic Stem Cell Derived Exosomes Revive Endogenous Repair Mechanisms in Failing Heart [Jul. 18, 2014]) (Year: 2014).*
Khan et al. (Circulation Research. Jun. 19, 2015; 117(1): 52-64) (Year: 2015).*
Temple University School of Medicine. Jun. 17, 2015. "Research Team Led by Temple's Raj Kishore, PhD, Uses Stem Cell Exosomes to Induce Damaged Mouse Hearts to Repair Themselves Without Stem Cell Risk" (https://medicine.temple.edu/news/research-team-led-temples-raj-kishore-phd-uses-st (Year: 2015).*
Cao et al., "miR-290/371-Mbd2-Myc circuit regulates glycolytic metabolism to promote pluripotency," EMBO J, Mar. 4, 2015;34(5):609-23.
Chen and Wang, "microRNAs in cardiovascular development," J Mol Cell Cardiol, May 2012;52(5):949-57.
Chen et al., "Targeted deletion of Dicer in the heart leads to dilated cardiomyopathy and heart failure," Proc Natl Acad Sci U S A. 2008;105:2111-2116.
Gruber et al., "Embryonic stem cell-specific microRNAs contribute to pluripotency by inhibiting regulators of multiple differentiation pathways," Nucleic Acids Res, Aug. 2014;42(14):9313-26.
Hanina et al., "Genome-wide identification of targets and function of individual MicroRNAs in mouse embryonic stem cells," PLoS Genet, Oct. 21, 2010;6(10):e1001163.
Joshi et al., "A cardiac myocyte-restricted Lin28/let-7 regulatory axis promotes hypoxia-mediated apoptosis by inducing the AKT signaling suppressor PIK3IP1," Biochimica et Biophysica Acta, 2015, 240-251.
Kishore et al. "More Than Tiny Sacks," Circulation Research, Jan. 22, 2016, vol. 118, Iss. 2, pp. 330-343.
Landgraf et al., "A mammalian microRNA expression atlas based on small RNA library sequencing," Cell. 2007;129:1401-1414.
Melton et al., "Opposing microRNA families regulate self-renewal in mouse embryonic stem cells," Nature, Feb. 4, 2010;463(7281):621-6.
Mohsin et al., "Rejuvenation of human cardiac progenitor cells with Pim-1 kinase," Circ Res, Oct. 25, 2013;113 (10):1169-79.
Peng et al., "Genome-Wide Studies Reveal That Lin28 Enhances the Translation of Genes Important for Growth and Survival of Human Embryonic Stem Cells," Stem Cells. Mar. 2011;29(3):496-504.
Porrello et al., "Transient Regenerative Potential of the Neonatal Mouse Heart," Science. Feb. 25, 2011; 331 (6020): 1078-1080.
Rao et al., "Loss of cardiac microRNA-mediated regulation leads to dilated cardiomyopathy and heart failure," Circ Res, Sep. 11, 2009;105(6):585-94.

(Continued)

*Primary Examiner* — Scott Long
(74) *Attorney, Agent, or Firm* — Riverside Law LLP

(57) ABSTRACT

The invention provides one or more of miR-290 family and Lin28a modified cardiac progenitor cell based therapies for the treatment of myocardial infarction. Exosomes derived from one or more of miR-290 family and Lin28a modified cardiac progenitor cells can also be used in cardiac therapy.

4 Claims, 21 Drawing Sheets

(56) References Cited

OTHER PUBLICATIONS

Sen et al. "miRNA Control of Tissue Repair and Regeneration," The American Journal of Pathology, Oct. 31, 2015, vol. 185, Iss. 10, pp. 2629-2640.

Shyh-Chang and Daley, "Lin28: primal regulator of growth and metabolism in stem cells," Cell Stem Cell, Apr. 4, 2013;12(4):395-406.

Shyh-Chang et al., "Lin28 Enhances Tissue Repair by Reprogramming Cellular Metabolism," Cell, 2013, 155:778-792.

Sirish et al., "MicroRNA profiling predicts a variance in the proliferative potential of cardiac progenitor cells derived from neonatal and adult murine hearts," J Mol Cell Cardiol. 2012;52:264-272.

Sluijter et al., "MicroRNA-1 and -499 regulate differentiation and proliferation in human-derived cardiomyocyte progenitor cells," Arterioscler Thromb Vasc Biol. 2010;30:859-868.

Tang et al., "Cardiac Progenitor Cells and Bone Marrow-Derived Very Small Embryonic-Like Stem Cells for Cardiac Repair After Myocardial Infarction," Circ J, 2010, 74:390-404.

Thum et al., "MicroRNAs in the human heart: a clue to fetal gene reprogramming in heart failure," Circulation, Jul. 17, 2007;116(3):258-67.

Torella et al., "Cardiac stem cell and myocyte aging, heart failure, and insulin-like growth factor-1 overexpression," Circ Res, Mar. 5, 2004;94(4):514-24.

Van Rooij et al., "A signature pattern of stress-responsive microRNAs that can evoke cardiac hypertrophy and heart failure," Proc Natl Acad Sci U S A. 2006;103:18255-18260.

Wang et al., "Embryonic stem cell-specific microRNAs regulate the G1-S transition and promote rapid proliferation," Nat Genet, Dec. 2008;40(12):1478-83.

Yu et al., "Induced Pluripotent Stem Cell Lines Derived from Human Somatic Cells," Science, 2007 318:1917-1920.

Yuan et al., "Lin28b reprograms adult bone marrow hematopoietic progenitors to mediate fetal-like lymphopoiesis," Science. Mar. 9, 2012;335(6073):1195-200.

Zhang et al., "Lin28a protects against cardiac ischaemia/reperfusion injury in diabetic mice through the insulin-PI3K-mTOR pathway," J Cell Mol Med, 2015, 1174-1182.

Zhang et al., "Lin28a protects against hypoxia/reoxygenation induced cardiomyocytes apoptosis by alleviating mitochondrial dysfunction under high glucose/high fat conditions," PLoS One. Oct. 14, 2014;9(10):e110580.

Zovoilis et al., "Members of the miR-290 cluster modulate in vitro differentiation of mouse embryonic stem cells," Differentiation, Sep.-Oct. 2009;78(2-3):69-78.

\* cited by examiner

MICRORNA-294 AND LIN28A AS A DRIVER OF CARDIAC TISSUE PROLIFERATION IN RESPONSE TO PATHOLOGICAL INJURY

CROSS-REFERENCE TO RELATED APPLICATIONS

This application is the U.S. national phase application filed under 35 U.S.C. § 371 claiming benefit to International Patent Application No. PCT/US2017/027876, filed on Apr. 17, 2017, which is entitled to priority under 35 U.S.C. § 119(e) to U.S. provisional application No. 62/323,002, filed Apr. 15, 2016, the disclosures of which are incorporated herein by reference in their entirety.

STATEMENT REGARDING FEDERALLY SPONSORED RESEARCH OR DEVELOPMENT

This invention was made with government support under RO1-HL126186 awarded by the National Institutes of Health (NIH). The government has certain rights in the invention.

BACKGROUND OF THE INVENTION

Cardiac repair in response to injury has been one of the main goals of regenerative medicine. Existing therapies for the treatment of heart failure patients are designed to be preventive and are unable to restore lost myocardium to injury. As a result, heart undergo adverse remodeling that ultimately leads to heart failure and death in the affected patients.

Despite the advances made in the art for cardiac repair, there is a need in the art for improved compositions and methods for treating cardiac disorders, diseases, and conditions. The present invention fulfills these needs.

SUMMARY OF THE INVENTION

In one embodiment, the invention relates to a composition comprising a modified cardiac progenitor cell (CPC), wherein the CPC has been modified with an activator of Lin28a. In one embodiment, the activator of Lin28a is one or more of a nucleic acid molecule encoding Lin28a and a peptide comprising Lin28a.

In one embodiment, the activator of Lin28a is one or more of a miR, pre-miR and miR-mimic. In one embodiment, the miR is a selected from the group consisting of miR-290a, miR-291a, miR-291b, miR-292a, miR-293, miR-294, miR-295, miR-371a, miR-371b, miR-372, miR-302b and a combination thereof.

In one embodiment, the CPC is autologous, allogeneic, syngeneic, or xenogeneic to a subject having a cardiac disease, disorder or injury. In one embodiment, the cardiac disease, disorder or injury is myocardial infarction.

In one embodiment, the invention relates to a composition comprising an exosome derived from a modified CPC, wherein the CPC has been modified with an activator of Lin28a. In one embodiment, the activator of Lin28a is one or more of a nucleic acid molecule encoding Lin28a and a peptide comprising Lin28a. In one embodiment, the activator of Lin28a is one or more of a miR, pre-miR and miR-mimic.

In one embodiment, the miR is a selected from the group consisting of miR-290a, miR-291a, miR-291b, miR-292a, miR-293, miR-294, miR-295, miR-371a, miR-371b, miR-372, miR-302b and a combination thereof.

In one embodiment, the CPC is autologous, allogeneic, syngeneic, or xenogeneic to a subject having a cardiac disease, disorder or injury. In one embodiment, the cardiac disease, disorder or injury is myocardial infarction.

In one embodiment, the invention relates to a method of treating a cardiac disease, disorder or injury in a subject, the method comprising administering to a subject in need thereof an effective amount of a composition comprising a modified CPC, or an exosome derived therefrom, wherein the CPC has been modified with an activator of Lin28a.

In one embodiment, the activator of Lin28a is one or more of a nucleic acid molecule encoding Lin28a and a peptide comprising Lin28a.

In one embodiment, the activator of Lin28a is one or more of a miR, pre-miR and miR-mimic. In one embodiment, the miR is one or more of miR-290a, miR-291a, miR-291b, miR-292a, miR-293, miR-294, miR-295, miR-371a, miR-371b, miR-372, miR-302b and a combination thereof.

In one embodiment, the CPC is autologous, allogeneic, syngeneic, or xenogeneic to a subject having a cardiac disease, disorder or injury. In one embodiment, the cardiac disease, disorder or injury is myocardial infarction.

In one embodiment, the composition is administered to the subject by one or more route selected from local, topical, subcutaneous, intravenous, oral, intramuscular, and a combination thereof. In one embodiment, the subject is a human.

BRIEF DESCRIPTION OF THE DRAWINGS

The following detailed description of exemplary embodiments of the invention will be better understood when read in conjunction with the appended drawings. For the purpose of illustrating the invention, there are shown in the drawings exemplary embodiments. It should be understood, however, that the invention is not limited to the precise arrangements and instrumentalities of the embodiments shown in the drawings.

FIG. 16, comprising FIG. 16A depicts experimental results demonstrating a decrease in miR-291 expression during development. FIG. 16B depicts experimental results demonstrating a decrease in miR-294 expression during development.

FIG. 17, comprising FIG. 17A depicts exemplary images demonstrating that there was increased p-histone+ cardiomyocytes 24 hrs after treatment with miR-294 mimic compared to negative control mimic. FIG. 17B depicts the results of the quantification of the levels of p-histone+ cardiomyocytes. FIG. 17C depict exemplary images demonstrating that there was increased Ki67 in miR-294 treated NRCMs compared to control cells. FIG. 17D depicts the results of the quantification of the levels of Ki67. FIG. 17E depict exemplary images demonstrating that there was enhanced cytokinesis in miR-294 treated NRCMs compared to control cells as evidenced by an increase in Aurora B staining. FIG. 17E depicts the results of the quantification of the levels of Aurora B staining.

FIG. 18, comprising FIG. 18A depicts the results of exemplary experiments demonstrating repression of Wee1 and upregulation of cell cycle markers by miR-294 in NRCMs. FIG. 18B depicts the results of exemplary experiments demonstrating luciferase assay validates Wee1 as miR-294 target. FIG. 18C depicts the results of exemplary experiments demonstrating RNA levels of miR-294 targets Wee1 and cell cycle markers in NRCMs as determined by qRT-PCR.

FIG. 19, comprising FIG. 19A depicts exemplary images demonstrating that there was increased p-histone+ adult feline cardiomyocytes after treatment with miR-294 compared to a control. FIG. 19B depicts the results of the quantification of the levels of p-histone+ cardiomyocytes. FIG. 19C depicts exemplary experimental results demonstrating that there was an increased % of mono-nucleated cells in adult myocytes treated with miR-294 along with a corresponding reduction in bi-nucleated cells.

FIG. 20, comprising FIG. 20A depicts exemplary experimental results demonstrating that there is enhanced cell cycle progression after miR-294 treatment. FIG. 20A depicts exemplary experimental results demonstrating that there is increased AKT phosphorylation after miR-294 treatment. FIG. 20C depicts exemplary experimental results demonstrating that there is decreased Annexin-V+ cells after miR-294 treatment. FIG. 20D depicts exemplary experimental results demonstrating miR-294 drives Lin28 expression. FIG. 20E depicts exemplary experimental results demonstrating that CPCs treated with miR-294 show an increase in proliferation. FIG. 20F depicts exemplary experimental results demonstrating that CPCs treated with miR-294 have increased PDK4 levels. FIG. 20G depicts exemplary experimental results demonstrating that CPCs treated with miR-294 have decreased population doubling times.

FIG. 21, comprising FIG. 21A depicts exemplary experimental results demonstrating increased ejection fraction (EF) and fractional shortening (FS) in the hearts treated with miR-294 compared to control miR treated animals 8 weeks after administration. FIG. 21B depicts exemplary experimental results demonstrating that miR-294 treated hearts demonstrated significant reduction in infarct size compared to controls 8 weeks after infarction. FIG. 21C depicts exemplary experimental results demonstrating enhanced c-kit+ CPCs in the heart with miR-294 treatment, along with the corresponding quantification. FIG. 21D depicts exemplary experimental results demonstrating that there are an increased number of BrdU+/sarcomeric actin+ cells in the heart treated with miR-294 compared to control animals, along with corresponding quantification.

DETAILED DESCRIPTION OF THE INVENTION

Figure 1:
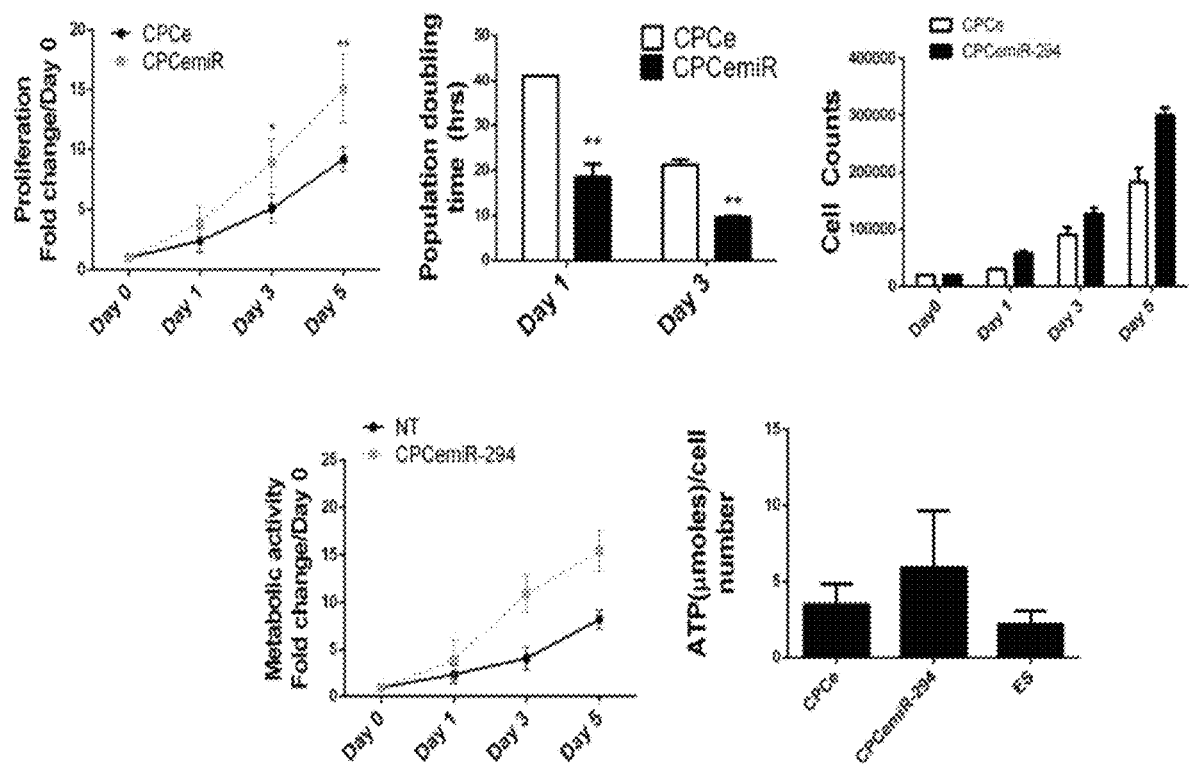
FIG. 1 depicts the results of exemplary experiments demonstrating that miR-294 augments CPC proliferation and cell cycle

The developmental heart is characteristic of rapidly dividing cardiomyocytes required to build a working myocardium. In contrast, adult heart has limited ability for cellular replacement resulting in the development of scar tissue to replace dead myocardium. Cardiac progenitor cells (CPC)

based therapy has been used as an alternative for cardiac repair but has been limited due to decreased repair potential of CPCs derived from heart failure patients.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of 20%, ±10%, ±5%, ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

"Antisense," as used herein, refers to a nucleic acid sequence which is complementary to a target sequence, such as, by way of example, complementary to a target miRNA sequence, including, but not limited to, a mature target miRNA sequence, or a sub-sequence thereof. Typically, an antisense sequence is fully complementary to the target sequence across the full length of the antisense nucleic acid sequence.

The term "body fluid" or "bodily fluid" as used herein refers to any fluid from the body of an animal. Examples of body fluids include, but are not limited to, plasma, serum, blood, lymphatic fluid, cerebrospinal fluid, synovial fluid, urine, saliva, mucous, phlegm and sputum. A body fluid sample may be collected by any suitable method. The body fluid sample may be used immediately or may be stored for later use. Any suitable storage method known in the art may be used to store the body fluid sample: for example, the sample may be frozen at about −20° C. to about −70° C. Suitable body fluids are acellular fluids. "Acellular" fluids include body fluid samples in which cells are absent or are present in such low amounts that the miRNA level determined reflects its level in the liquid portion of the sample, rather than in the cellular portion. Such acellular body fluids are generally produced by processing a cell-containing body fluid by, for example, centrifugation or filtration, to remove the cells. Typically, an acellular body fluid contains no intact cells however, some may contain cell fragments or cellular debris. Examples of acellular fluids include plasma or serum, or body fluids from which cells have been removed.

As used herein, "cardiac diseases or disorders" or "cardiovascular diseases or disorders" refer to any type of heart disease or disorders including cardiomyopathy, hypertrophic cardiomyopathy, dilated cardiomyopathy, diabetic cardiomyopathy, atherosclerosis, coronary artery disease, ischemic heart disease, myocarditis, viral infection, wounds, hypertensive heart disease, valvular disease, congenital heart disease, myocardial infarction, congestive heart failure, arrhythmias, diseases resulting in remodeling of the heart, heart failure, ischemia, myocardial infarction, transplantation, hypertension, restenosis, angina pectoris, rheumatic heart disease, injuries-physical or otherwise, or congenital cardiovascular defects. Diseases or disorders of the hem can be due to any reason, such as for example, damage to cardiac tissue such as a loss of contractility (e.g., as might be demonstrated by a decreased ejection fraction).

Cardiac damage or injury characterized by insufficient cardiac function includes any impairment or absence of a normal cardiac function or presence of an abnormal cardiac function. Abnormal cardiac function can be the result of disease, injury, and/or aging. As used herein, abnormal cardiac function includes morphological and/or functional abnormality of a cardiomyocyte, a population of cardiomyocytes, or the heart itself. Non-limiting examples of morphological and functional abnormalities include physical deterioration and/or death of cardiomyocytes, abnormal growth patterns of cardiomyocytes, abnormalities in the physical connection between cardiomyocytes, under- or over-production of a substance or substances by cardiomyocytes, failure of cardiomyocytes to produce a substance or substances which they normally produce, and transmission of electrical impulses in abnormal patterns or at abnormal times. Abnormalities at a more gross level include dyskinesis, reduced ejection fraction, changes as observed by echocardiography (e.g., dilatation), changes in EKG, changes in exercise tolerance, reduced capillary perfusion, and changes as observed by angiography. Abnormal cardiac function is seen with many disorders including, for example, ischemic heart disease, e.g., angina pectoris, myocardial infarction, chronic ischemic hem disease, hypertensive heart disease, pulmonary heart disease (cor pulmonale), valvular heart disease, e.g., rheumatic fever, mitral valve prolapse, calcification of mitral annulus, carcinoid heart disease, infective endocarditis, congenital heart disease, myocardial disease, e.g., myocarditis, dilated cardiomyopathy, hypertensive cardiomyopathy, diabetic cardiomyopathy, cardiac disorders which result in congestive heart failure, and tumors of the hem, e.g., primary sarcomas and secondary tumors. Heart damage or injury also includes wounds, such as for example, knife wound; biological (e.g. viral; autoimmune diseases) or chemical (e.g. chemotherapy, drugs); surgery; transplantation and the like.

As used herein, the phrase "heart failure" refers to a condition in which the heart cannot pump blood efficiently to the rest of the body. Heart failure may be due to damage to the heart or narrowing of the arteries due to infarction, cardiomyopathy (primary or secondary), hypertension, diabetes, coronary artery disease, valve disease, birth defects or infection. Heart failure can further be described as chronic, congestive, acute, decompensated, systolic or diastolic. The New York Heart Association (NYHA) classification describes the severity of the disease based on functional capacity of the patient; NYHA class can progress and/or regress based on treatment or lack of response to treatment in heart failure, "increased severity" of cardiovascular disease refers to the worsening of disease as indicated by increased NYHA classification, to, for example, Class III or Class IV, and "reduced severity" of cardiovascular disease refers to an improvement of the disease as indicated by reduced NYHA classification, from, for example, class III or IV to class II or I.

"Myocardial ischemia" refers to a lack of oxygen flow to the heart which results in myocardial ischemic damage. As used herein, the phrase myocardial ischemic damage includes damage caused by reduced blood flow to the myocardium. Non-limiting examples of causes of myocardial ischemia and myocardial ischemic damage include: decreased aortic diastolic pressure, increased intraventricular pressure and myocardial contraction, coronary artery stenosis (e.g., coronary ligation, fixed coronary stenosis, acute plaque change (e.g., rupture, hemorrhage), coronary artery thrombosis, vasoconstriction), aortic valve stenosis and regurgitation, and increased right atrial pressure. Non-limiting examples of adverse effects of myocardial ischemia and myocardial ischemic damage include: myocyte damage (e.g., myocyte cell loss, myocyte hypertrophy, myocyte cellular hyperplasia), angina (e.g., stable angina, variant angina, unstable angina, sudden cardiac death), myocardial infarction, and congestive heart failure. Damage due to myocardial ischemia may be acute or chronic, and consequences may include scar formation, cardiac remodeling, cardiac hypertrophy, wall thinning, dilatation, and associated functional changes. The existence and etiology of acute or chronic myocardial damage and/or myocardial ischemia may be diagnosed using any of a variety of methods and techniques well known in the art including, e.g., non-invasive imaging (e.g., MRI, echocardiography), angiography, stress testing, assays for cardiac-specific proteins such as cardiac troponin, and clinical symptoms. These methods and techniques as well as other appropriate techniques may be used to determine which subjects are suitable candidates for the treatment methods described herein.

The term "clinical factors" as used herein, refers to any data that a medical practitioner may consider in determining a diagnosis of disease. Such factors include, but are not limited to, the patient's medical history, a physical examination of the patient, results of a CT scan, complete blood count, analysis of the activity of enzymes, examination of cells, cytogenetics, and immunophenotyping of blood cells.

"Complementary" as used herein refers to the broad concept of subunit sequence complementarity between two nucleic acids. When a nucleotide position in both of the molecules is occupied by nucleotides normally capable of base pairing with each other, then the nucleic acids are considered to be complementary to each other at this position. Thus, two nucleic acids are substantially complementary to each other when at least about 50%, at least about 60% or at least about 80% of corresponding positions in each of the molecules are occupied by nucleotides which normally base pair with each other (e.g., A:T and G:C nucleotide pairs).

As used herein, the term "diagnosis" means detecting a disease or disorder or determining the stage or degree of a disease or disorder. Usually, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease; i.e. there may be differential diagnoses that can be inferred from a diagnostic factor or symptom. Likewise, there may be instances where a factor or symptom that is indicative of a particular disease is present in an individual that does not have the particular disease. The diagnostic methods may be used independently, or in combination with other diagnosing and/or staging methods known in the medical art for a particular disease or disorder.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

As used herein "endogenous" refers to any material from or produced inside an organism, cell, tissue or system.

The term "expression" as used herein is defined as the transcription and/or translation of a particular nucleotide sequence.

"Exosomes" as used herein are plasma particles shed from eukaryotic cells that are formed by exocytic budding due to activation or apoptosis, and are indicative of cell damage. As contemplated herein, exosomes derived from a parent cell (e.g., a cardiac progenitor cell (CPC)) may contain miRNA, proteins and other antigens from their parent cell and are often pro-coagulative and pro-inflammatory.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology.

As used herein, "homology" is used synonymously with "identity."

"Inhibitors" and "activators" as used herein, refer to activating or inhibitory molecules of expression or activity of a biological molecule (e.g., a gene, protein, mRNA or miR of interest). Inhibitors are compounds that, e.g., bind to, partially or totally block activity, decrease, prevent, delay activation, inactivate, desensitize, or down regulate the level, activity or expression of a biological molecule. "Activators" are compounds that increase, open, activate, facilitate, enhance activation, sensitize, agonize, or up regulate the level, activity or expression of a biological molecule, e.g., agonists. Inhibitors or activators also include genetically modified versions of a biological molecule, e.g., versions with altered activity, as well as naturally occurring and synthetic ligands, antagonists, agonists, antibodies, peptides, cyclic peptides, nucleic acids, antisense molecules, ribozymes, RNAi, microRNA, and siRNA molecules, small organic molecules and the like.

As used herein, "isolated" means altered or removed from the natural state through the actions, directly or indirectly, of a human being. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's clinical parameters.

As used herein, "microRNA," "miRNA," or "miR" describes small non-coding RNA molecules, generally about 15 to about 50 nucleotides in length, in one embodiment about 17-23 nucleotides in length, which can play a role in regulating gene expression through, for example, a process termed RNA interference (RNAi). RNAi describes a phenomenon whereby the presence of an RNA sequence that is complementary or antisense to a sequence in a target gene messenger RNA (mRNA) results in inhibition of expression of the target gene. miRNAs are processed from hairpin precursors of about 70 or more nucleotides (pre-miRNA) which are derived from primary transcripts (pri-miRNA) through sequential cleavage by RNAse III enzymes. miR-Base is a comprehensive microRNA database located at www.mirbase.org, incorporated by reference herein in its entirety for all purposes.

"Naturally occurring" as used herein describes a composition that can be found in nature as distinct from being artificially produced. For example, a nucleotide sequence present in an organism, which can be isolated from a source in nature and which has not been intentionally modified by a person, is naturally occurring.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

As used herein, "polynucleotide" includes cDNA, RNA, DNA/RNA hybrid, anti-sense RNA, siRNA, miRNA, genomic DNA, synthetic forms, and mixed polymers, both sense and antisense strands, and may be chemically or biochemically modified to contain non-natural or derivatized, synthetic, or semi-synthetic nucleotide bases. Also, included within the scope of the invention are alterations of a wild type or synthetic gene, including but not limited to deletion, insertion, substitution of one or more nucleotides, or fusion to other polynucleotide sequences.

"Cardiac Progenitor cell" (CPC) as used herein may include any type of CPC understood by those skilled in the art, including c-Kit+ CPCs; cardiospheres/cardiosphere-derived cells (CDCs); epicardium derived cells; cardiac side population cells (identified by their ability to exclude Hoechst dye from nuclei); stem cell antigen-1 (Sca-1+) CPCs; Islet-1 (Isl-1+) expressing CPCs and platelet derived growth factor receptor-alpha (PDGFRα+) expressing CPCs.

The term "recombinant DNA" as used herein is defined as DNA produced by joining pieces of DNA from different sources.

"Sample" or "biological sample" as used herein means a biological material isolated from an individual. The biological sample may contain any biological material suitable for detecting the desired markers, and may comprise cellular and/or non-cellular material obtained from the individual.

The terms "subject," "patient," "individual," and the like are used interchangeably herein, and refer to any animal, or cells thereof whether in vitro or in situ, amenable to the methods described herein. In certain non-limiting embodiments, the patient, subject or individual is a human.

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

In one embodiment, the invention relates to a composition and method for treatment of cardiac injury whereby cardiac progenitor cells (CPC) or exosomes from CPCs are treated with miR-294 are provided to a subject in need thereof.

In one embodiment, the invention relates to a composition and method for treatment of cardiac injury whereby CPCs or exosomes from CPCs wherein Lin28a has been activated are provided to a patient in need thereof.

In one embodiment, the present invention provides therapeutic compositions and methods for the treatment of a cardiac disease, cardiac disorder or cardiac injury. In various embodiments, the therapeutic compositions and methods comprise a modified CPC or exosome derived therefrom.

miR-290 Gene Family

The invention is based in part on results presented herein demonstrating that miR-294 is expressed in the heart during development and is lost in the neonates and adults as confirmed by qRT-PCR. However CPCs treated with miR-294 by mimic and lentiviral modification based approaches showed increased proliferation, cell cycle progression and survival. Further, neonatal ventricular cardiomyocytes (NRVMs) treated with miR-294 mimic showed elevated mRNA levels of cell cycle markers (E2F family and cyclins)

concurrent with increased expression of p-histone 3, Ki67 and Aurora B kinase (G2/M) as confirmed by immunocytochemistry compared to control cells. AAV-9 carrying miR-294 was administered in mice subjected to myocardial infarction augmented cardiac function 8 weeks after injury. Increase myocyte proliferation was observed in the heart after miR-294 treatment as analyzed by BrdU uptake, p-Histone 3 and Aurora B expression by immunostaining. Concurrently, a decrease in infarct size along with decreased apoptosis was observed in the miR-294 hearts compared to the control. Furthermore, increased c-kit+ CPCs activation and proliferation was observed in the miR-294 receiving hearts. In conclusion, ectopic expression of miR-294 recapitulates embryonic signaling and enhances cardiomyocyte ability to proliferate together with CPC activation and expansion leading to augmented cardiac function in mice after myocardial infarction.

The present invention is based partly on the discovery of the role of the miR-290 gene family in myocardial biology, cardiac tissue proliferation and CPC/stem cell function. The miR-290 gene family is a closely related family of miR with homologs and orthologs in multiple species. Members of the miR gene family include, but are not limited to, miR-290a, miR-291a, miR-291b, miR-292a, miR-293, miR-294, miR-295, miR-371a, miR-371b, and miR-372. Orthologs of the miR-290 family include, but are not limited to hsa-miR-302. In one embodiment, the invention relates to compositions and methods relating to the use of miR-302b and miR-372, which share the same seed sequence as miR-294, in treating a cardiac disease, disorder or injury.

In one embodiment, the invention relates to composition and methods relating to modified CPCs expressing or more member of the miR-290 gene family or a homolog or ortholog thereof, which drives cardiac proliferative response leading to augmentation of cardiac function after myocardial infarction.

In one embodiment, the invention provides composition and methods directed to the use of one or more one or more member of the miR-290 gene family family or a homolog or ortholog thereof as a novel therapeutic system aiming to enhance CPC function and their effectiveness to repair the heart together with augmenting cardiac tissue proliferative properties. In one embodiment, introduction of one or more member of the miR-290 gene family, or a mimic thereof, provides an effective treatment for promoting endogenous repair capability of the heart. In some embodiments, one or more miR, pre-miR, or miR mimic are provided as therapeutic agents for the treatment of cardiac injury.

Lin28a

Lin28a has been implicated in reprogramming tissue repair and regeneration together with enhancing expression of mRNA targets for proliferation, survival and metabolism. Nevertheless, there are no reports showing the role of miR-294-Lin28a axis in the context of the heart. The invention is based in part on results presented herein demonstrating that miR-294 and Lin28a mRNA expression coincides during embryonic heart development and declines rapidly after birth with complete abrogation in the 3 week old adult heart.

In one embodiment, the invention is partly based on the discovery that miR-294 drives Lin28a expression. Increased Lin28a expression was observed in CPCs, neonatal rat cardiomyocytes (NRCMs) and adult cardiomyocytes both at the protein and mRNA level after treatment with miR-294 compared to control treated cells. Alternatively, miR-294 expressing CPCs treated with antagomiR for miR-294 had decreased protein levels of Lin28a compared to control treated cells. Moreover, miR-294 administered hearts showed increased Lin28a mRNA expression confirming correlation with miR-294 and Lin28a. CPCs were lentivirally engineered to express Lin28a to determine its effect on CPC function. Increased mRNA expression of glycolytic and fatty acid oxidation enzymes was observed in the cells together with increased ATP content and maximal respiration in CPCs overexpressing Lin28a compared to control indicating higher metabolic rates. Lin28a CPC demonstrated increased proliferation as measured by CyQuant assay and increased survival in response to H2O2 stress compared to controls. To test whether therapeutic efficacy of Lin28a, human CPCs were engineered to express Lin28a and exosome from Lin28a human CPCs were isolated. Analysis of Lin28a human CPC exosomes showed increased mRNA expression of Lin28a along with upregulation of survival genes compared to control exosomes. Therefore, the invention is based in part on the discovery that Lin28a is a target of miR-294 that may have implications for cardiac repair.

CPC Therapy

Cardiac progenitor cell (CPC) based therapy has moved into clinics demonstrating safety of the cells yet effects on cardiac function are minimal. A number of reasons limit CPC performance including patient age and disease etiology meriting the need for alternate strategies to enhance CPC efficacy for cardiac repair.

Augmentation of CPC and cardiac tissue function would allow restoration of cardiac function in response to pathological injury. In one embodiment, the invention provides modified Cardiac progenitor cell based therapies for the treatment of cardiac injury, where the CPC has been modified with one or more member of the miR-290 gene family, a target thereof or a mimic thereof. In one embodiment, the invention relates to exosomes derived from modified CPCs and their use as a therapeutic for the treatment of cardiac injury.

Therefore, in one embodiment, the invention provides a strategy based on activating developmental signaling in CPCs via introduction of one or more of hsa-miR-371a, hsa-miR-371b and hsa-miR-372, or a mimic thereof to enhance CPC function and the ability to repair the heart. In one embodiment, the invention provides a strategy based on activating developmental signaling in CPCs via introduction of Lin28a to enhance CPC function and the ability to repair the heart.

In one embodiment, the invention is based on using exosome derived from human CPCs overexpressing Lin28a to as a therapeutic for treatment of cardiac injury. In one embodiment, the invention is based on using exosome derived from human CPCs modified with one or more of hsa-miR-371a, hsa-miR-371b and hsa-miR-372, or a mimic thereof as a therapeutic for treatment of cardiac injury.

In one embodiment, the invention provides modified CPC based therapies for the treatment of myocardial infarction.

In one embodiment, the invention provides exosomes derived from human CPCs modified with Lin28a. In one embodiment, the instant invention allows the development of a translational therapy for the treatment of heart failure patients.

Methods of Obtaining and Culturing CPCs of the Invention

The CPCs of the invention can be obtained from any animal by any suitable method. A first step in any such method requires the isolation of CPCs from the source animal. The animal can be alive or dead, so long as the CPCs are viable.

CPCs of the invention can be isolated from heart tissue. Typically, human CPCs are obtained from a biopsy sample from a living donor. CPCs can be isolated using methods known in the art. Exemplary methods for isolating CPCs from biopsy samples are described in (Choi et al., 2013, Transplant Proc, 45:420-426) which is incorporated herein in its entirety.

In one embodiment, the isolated CPCs are resuspended and can be washed (e.g. in PBS). Cells can be centrifuged and resuspended successive times to achieve a greater purity. In one embodiment, the isolated CPCs cells may be a heterogeneous population of cells which includes the CPCs of the invention. Several CPC populations have been reported in the developing and adult heart including: c-Kit+ CPCs; cardiospheres/cardiosphere-derived cells (CDCs); epicardium derived cells; cardiac side population cells (identified by their ability to exclude Hoechst dye from nuclei); stem cell antigen-1 (Sca-1+) CPCs; Islet-1 (Isl-1+) expressing CPCs and platelet derived growth factor receptor-alpha (PDGFRα+) expressing CPCs. CPCs may be separated from other cells by methods that include, but are not limited to, cell sorting, size fractionation, granularity, density, molecularity, morphologically, and immunohistologically. In one embodiment, CPCs of the invention are separated from other cells immunohistochemically, for example, by panning, using magnetic beads, or affinity chromatography. In one embodiment, CPCs can be separated through positive and/or negative selection of one or more of expressed markers located on the surface of the CPCs. For example, in one embodiment, expressed markers of c-Kit+ CPCs include, but are not limited to c-Kit+, CD34−, CD45−, Sca-1+, Abcg2+, CD105+, CD166+, GATA4+, NKX2-5+/−, MEF2C+. In one embodiment, expressed markers of Sca1+ CPCs include, but are not limited to, Sac-1+, CD105+, CD34−, CD45−, FLK1−, c-Kit+/−, GATA4+, NKX2-5+/1, MEF2C+. Accordingly, separation of CPCs may be carried out through positive selection, negative selection, or depletion. Such methods are well known in the art.

The isolated CPCs can be expanded or cultured according to known methods. In one embodiment, the CPCs can be cultured in vitro to maintain a source of CPCs. In one embodiment, the CPCs can be induced to differentiate into a cardiac cell type.

The CPCs can be cultured and, if desired, assayed for number and viability, to assess the yield. In one embodiment, the stem cells are cultured without differentiation using standard cell culture media (e.g., DMEM, typically supplemented with 5-15% (e.g., 10%) serum (e.g., fetal bovine serum, horse serum, etc.). In one embodiment, the stem cells are passaged at least one time in such medium without differentiating, while still retaining their developmental phenotype. In one embodiment, the CPCs are passaged in vitro at least 1 time, at least 2 times, at least 3, times, at least 4 times, at least 5 times or more than 5 times.

In one embodiment, all cells extracted from a sample are cultured. To culture the cells, the cells may be plated at a desired density, such as between about 100 cells/cm$^2$ to about 100,000 cells/cm$^2$ (such as about 500 cells/cm$^2$ to about 50,000 cells/cm$^2$, or between about 1,000 cells/cm$^2$ to about 20,000 cells/cm$^2$).

In one embodiment the extracted cells are plated at a lower density (e.g., about 300 cells/cm$^2$) to facilitate the clonal isolation of the CPCs. For example, after a few days, CPCs plated at such densities will proliferate (expand) into a clonal population of CPCs.

Any suitable method for cloning stem cell populations can be used to clone and expand a CPC population of the invention. The cloning and expanding methods include cultures of cells, or small aggregates of cells, physically picking and seeding into a separate plate (such as the well of a multi-well plate). Alternatively, the stem cells can be subcloned onto a multi-well plate at a statistical ratio for facilitating placing a single cell into each well (e.g., from about 0.1 to about 1 cell/well or even about 0.25 to about 0.5 cells/well, such as 0.5 cells/well). The CPCs can be cloned by plating them at low density (e.g., in a petri-dish or other suitable substrate) and isolating them from other cells using devices such as a cloning rings. Alternatively, where an irradiation source is available, clones can be obtained by permitting the cells to grow into a monolayer and then shielding one and irradiating the rest of cells within the monolayer. The surviving cell then will grow into a clonal population. Production of a clonal population can be expanded in any suitable culture medium.

In any event, whether clonal or not, the isolated CPCs can be cultured in a specific inducing medium to induce the CPCs to differentiate. The CPCs give rise to cells of multiple lineages, including endothelial cells (ECs), smooth muscle cells (SMC), and cardiomyocyte lineages. Thus, CPCs can be treated to differentiate into a variety of cell types.

In one embodiment, the CPCs of the invention can be induced to differentiate into a specific lineage by co-culturing the cells of the invention with mature cells, or precursors thereof. In an embodiment, induction of the CPCs into specific cell types by co-culturing with differentiated mature cells includes, but is not limited to, myogenic differentiation induced by co-culturing the CPCs with cardiomyocytes. Alternatively, the CPCs are cultured in a conditioned medium and induced to differentiate into a specific phenotype. Conditioned medium is medium which was cultured with a mature cell that provides cellular factors to the medium such as cytokines, growth factors, hormones, and extracellular matrix. For example, a medium that has been exposed to mature cardiomyocytes is used to culture and induce CPCs to differentiate into a myogenic lineage. Other examples of conditioned media inducing specific differentiation include, but are not limited to, culturing in a medium conditioned by exposure to heart valve cells to induce differentiation into heart valve tissue.

For co-culture, it may be desirable for the CPCs and the desired other cells to be co-cultured under conditions in which the two cell types are in contact. This can be achieved, for example, by seeding the cells as a heterogeneous population of cells onto a suitable culture substrate. Alternatively, the CPCs can first be grown to confluence, which will serve as a substrate for the second desired cells to be cultured within the conditioned medium.

Other methods of inducing differentiation are known in the art and can be employed to induce the CPCs to give rise to cells having a specific lineage. In one embodiment, such methods include culturing the cells in a differentiation medium comprising one or more factors that induce the CPCs to differentiation. The CPCs can be assayed to determine whether, in fact, they have acquired the desired lineage.

Methods to characterize differentiated cells that develop from the CPCs of the invention, include, but are not limited to, histological, morphological, biochemical and immunohistochemical methods, or using cell surface markers, or genetically or molecularly, or by identifying factors secreted by the differentiated cell, and by the inductive qualities of the differentiated CPCs.

In one embodiment, a population of CPCs comprises one or more additional co-cultured cell types. In other embodiments, the population is substantially homogeneous, consisting essentially of the inventive CPCs.

In one embodiment, the CPCs of the invention can be induced to differentiate prior to being introduced into the recipient by, for example, culturing the CPCs in a differentiating-inducing medium. In another embodiment, the CPCs of the invention are not induced to differentiate, but are introduced into the recipient as a substantially pure population of cells that may differentiate following introduction into the recipient.

The CPCs also can be induced to dedifferentiate into a developmentally more immature phenotype (e.g., a fetal or embryonic phenotype). Such an induction is achieved upon exposure of the CPCs to conditions that mimic those within fetuses and embryos. For example, the inventive CPCs, can be co-cultured with cells isolated from fetuses or embryos, or in the presence of fetal serum.

In one embodiment of the present invention, the CPC of the present invention is autologous. That is, a cell of the invention is procured from a donor and returned to the same individual after selection and expansion of said cell, i.e., donor and recipient are the same individual. In another embodiment of the present invention, the CPCs of the present invention are allogeneic. That is, the CPC of the invention is procured from a donor but administered to a different individual, i.e., the donor and recipient are genetically different individuals.

Methods of Obtaining Exosomes

Any method known in the art for isolating and purifying exosomes is appropriate for use in the method of the invention. Various methods for isolation of exosomes from biological fluids have been developed. They include, but are not limited to, centrifugation, chromatography, filtration, polymer-based precipitation and immunological separation (e.g. immunobeads).

Genetic Modification

In one embodiment, the CPCs may be treated with a nucleic acid encoding a protein, a peptide, a miR, or a fragment thereof. In one embodiment, the CPCs can be genetically modified, e.g., to express exogenous nucleic acid sequences. Therefore, the invention provides a method of genetically modifying such cells and populations. In one embodiment, an exogenous nucleic acid sequence encodes Lin28a. In one embodiment, an exogenous nucleic acid sequence encodes a member of the miR-290 gene family, a homolog thereof, an ortholog thereof, or a combination thereof. Therefore, in various embodiments the invention provides an isolated population of genetically modified CPCs comprising nucleic acid molecules for expression of Lin28a, miR-290a, miR-291a, miR-291b, miR-292a, miR-293, miR-294, miR-295, miR-371a, miR-371b, miR-372, miR-302b or a combination thereof, and methods of preparing and using genetically modified CPCs.

In one embodiment, the CPCs is exposed to a gene transfer vector comprising an exogenous nucleic acid sequence, such that the nucleic acid molecule is introduced into the cell under conditions appropriate for the exogenous nucleic acid sequence to be expressed within the cell. The exogenous nucleic acid sequence generally is an expression cassette, including a polynucleotide operably linked to a suitable promoter.

In the context of gene therapy, the cells of the invention can be treated with a nucleic acid molecule encoding Lin28a, miR-290a, miR-291a, miR-291b, miR-292a, miR-293, miR-294, miR-295, miR-371a, miR-371b, miR-372, miR-302b or a combination thereof prior to delivery of the cells into the recipient. In some cases, such cell-based gene delivery can present significant advantages of other means of gene delivery, such as direct injection of an adenoviral gene delivery vector. Delivery of a therapeutic nucleic acid molecule that has been pre-inserted into cells avoids the problems associated with penetration of gene therapy vectors into desired cells in the recipient.

Accordingly, the invention provides the use of genetically modified cells that have been cultured according to the methods of the invention. Genetic modification may, for instance, result in the expression of an exogenous nucleic acid sequence. Such genetic modification may have therapeutic benefit. Alternatively, or in addition, the genetic modification may provide a means to track or identify the cells so-modified, for instance, after administration of a composition of the invention into an individual. Tracking a cell may include tracking migration, assimilation and survival of a transplanted genetically-modified cell. Genetic modification may also include at least a second nucleic acid sequence. A second nucleic acid sequence may encode, for instance, a selectable antibiotic-resistance gene or another selectable marker.

The cells of the invention may be genetically modified using any method known to the skilled artisan. See, for instance, Sambrook et al. (2001, Molecular Cloning: A Laboratory Manual, Cold Spring Harbor Laboratory Press, Cold Spring Harbor, N.Y.). For example, a cell may be exposed to an expression vector comprising an exogenous nucleic acid sequence, such that the nucleic acid is introduced into the cell under conditions appropriate for the exogenous nucleic acid sequence to be expressed within the cell. In one embodiment, the polynucleotide can encode Lin28a, miR-290a, miR-291a, miR-291b, miR-292a, miR-293, miR-294, miR-295, miR-371a, miR-371b, miR-372, miR-302b or a combination thereof.

Nucleic acids can be of various lengths. Nucleic acid lengths typically range from about 20 nucleotides to 20 Kb, or any numerical value or range within or encompassing such lengths, 10 nucleotides to 10 Kb, 1 to 5 Kb or less, 1000 to about 500 nucleotides or less in length. Nucleic acids can also be shorter, for example, 100 to about 500 nucleotides, or from about 12 to 25, 25 to 50, 50 to 100, 100 to 250, or about 250 to 500 nucleotides in length, or any numerical value or range or value within or encompassing such lengths. Shorter polynucleotides are commonly referred to as "oligonucleotides" or "probes" of single- or double-stranded DNA.

Nucleic acids can be produced using various standard cloning and chemical synthesis techniques. Techniques include, but are not limited to nucleic acid amplification, e.g., polymerase chain reaction (PCR), with genomic DNA or cDNA targets using primers (e.g., a degenerate primer mixture) capable of annealing to antibody encoding sequence. Nucleic acids can also be produced by chemical synthesis (e.g., solid phase phosphoramidite synthesis) or transcription from a gene. The sequences produced can then be translated in vitro, or cloned into a plasmid and propagated and then expressed in a cell (e.g., a host cell such as yeast or bacteria, a eukaryote such as an animal or mammalian cell or in a plant).

Nucleic acids can be included within vectors as cell transfection typically employs a vector. The term "vector," refers to, e.g., a plasmid, virus, such as a viral vector, or other vehicle known in the art that can be manipulated by insertion or incorporation of a polynucleotide, for genetic manipulation (i.e., "cloning vectors"), or can be used to transcribe or translate the inserted polynucleotide (i.e., "expression vectors"). Such vectors are useful for introducing polynucleotides in operable linkage with a nucleic acid, and expressing the transcribed encoded protein in cells in vitro, ex vivo or in vivo.

A vector generally contains at least an origin of replication for propagation in a cell. Control elements, including expression control elements, present within a vector, are included to facilitate transcription and translation. The term "control element" is intended to include, at a minimum, one or more components whose presence can influence expression, and can include components other than or in addition to promoters or enhancers, for example, leader sequences and fusion partner sequences, internal ribosome binding sites (IRES) elements for the creation of multigene, or polycistronic, messages, splicing signal for introns, maintenance of the correct reading frame of the gene to permit in-frame translation of mRNA, polyadenylation signal to provide proper polyadenylation of the transcript of a gene of interest, stop codons, among others.

Vectors included are those based on viral vectors, such as retroviral (lentivirus for infecting dividing as well as non-dividing cells), foamy viruses (U.S. Pat. Nos. 5,624,820, 5,693,508, 5,665,577, 6,013,516 and 5,674,703; WO92/05266 and WO92/14829), adenovirus (U.S. Pat. Nos. 5,700,470, 5,731,172 and 5,928,944), adeno-associated virus (AAV) (U.S. Pat. No. 5,604,090), herpes simplex virus vectors (U.S. Pat. No. 5,501,979), cytomegalovirus (CMV) based vectors (U.S. Pat. No. 5,561,063), reovirus, rotavirus genomes, simian virus 40 (SV40) or papilloma virus (Cone et al., Proc. Natl. Acad. Sci. USA 81:6349 (1984); Eukaryotic Viral Vectors, Cold Spring Harbor Laboratory, Gluzman ed., 1982; Sarver et al., Mol. Cell. Biol. 1:486 (1981); U.S. Pat. No. 5,719,054). Adenovirus efficiently infects slowly replicating and/or terminally differentiated cells and can be used to target slowly replicating and/or terminally differentiated cells. Simian virus 40 (SV40) and bovine papilloma virus (BPV) have the ability to replicate as extra-chromosomal elements (Eukaryotic Viral Vectors, Cold Spring Harbor Laboratory, Gluzman ed., 1982; Sarver et al., Mol. Cell. Biol. 1:486 (1981)). Additional viral vectors useful for expression include reovirus, parvovirus, Norwalk virus, coronaviruses, paramyxo- and rhabdoviruses, togavirus (e.g., sindbis virus and semliki forest virus) and vesicular stomatitis virus (VSV) for introducing and directing expression of a polynucleotide or transgene in pluripotent stem cells or progeny thereof (e.g., differentiated cells).

Vectors including a nucleic acid can be expressed when the nucleic acid is operably linked to an expression control element. As used herein, the term "operably linked" refers to a physical or a functional relationship between the elements referred to that permit them to operate in their intended fashion. Thus, an expression control element "operably linked" to a nucleic acid means that the control element modulates nucleic acid transcription and as appropriate, translation of the transcript.

The term "expression control element" refers to nucleic acid that influences expression of an operably linked nucleic acid. Promoters and enhancers are particular non-limiting examples of expression control elements. A "promoter sequence" is a DNA regulatory region capable of initiating transcription of a downstream (3' direction) sequence. The promoter sequence includes nucleotides that facilitate transcription initiation. Enhancers also regulate gene expression, but can function at a distance from the transcription start site of the gene to which it is operably linked. Enhancers function at either 5' or 3' ends of the gene, as well as within the gene (e.g., in introns or coding sequences). Additional expression control elements include leader sequences and fusion partner sequences, internal ribosome binding sites (IRES) elements for the creation of multigene, or polycistronic, messages, splicing signal for introns, maintenance of the correct reading frame of the gene to permit in-frame translation of mRNA, polyadenylation signal to provide proper polyadenylation of the transcript of interest, and stop codons.

Expression control elements include "constitutive" elements in which transcription of an operably linked nucleic acid occurs without the presence of a signal or stimuli. For expression in mammalian cells, constitutive promoters of viral or other origins may be used. For example, SV40, or viral long terminal repeats (LTRs) and the like, or inducible promoters derived from the genome of mammalian cells (e.g., metallothionein IIA promoter; heat shock promoter, steroid/thyroid hormone/retinoic acid response elements) or from mammalian viruses (e.g., the adenovirus late promoter; mouse mammary tumor virus LTR) are used.

Expression control elements that confer expression in response to a signal or stimuli, which either increase or decrease expression of operably linked nucleic acid, are "regulatable." A regulatable element that increases expression of operably linked nucleic acid in response to a signal or stimuli is referred to as an "inducible element." A regulatable element that decreases expression of the operably linked nucleic acid in response to a signal or stimuli is referred to as a "repressible element" (i.e., the signal decreases expression; when the signal is removed or absent, expression is increased). Expression control elements include elements active in a particular tissue or cell type, referred to as "tissue-specific expression control elements." Tissue-specific expression control elements are typically more active in specific cell or tissue types because they are recognized by transcriptional activator proteins, or other transcription regulators active in the specific cell or tissue type, as compared to other cell or tissue types.

In accordance with the invention, there are provided CPCs and their progeny transfected with a nucleic acid or vector. Such transfected cells include but are not limited to a primary cell isolate, populations or pluralities of multipotent stem cells, cell cultures (e.g., passaged, established or immortalized cell line), as well as progeny cells thereof (e.g., a progeny of a transfected cell that is clonal with respect to the parent cell, or has acquired a marker or other characteristic of differentiation).

The nucleic acid or protein can be stably or transiently transfected (expressed) in the cell and progeny thereof. The cell(s) can be propagated and the introduced nucleic acid transcribed and protein expressed. A progeny of a transfected cell may not be identical to the parent cell, since there may be mutations that occur during replication.

Viral and non-viral vector means of delivery into CPCs, in vitro, in vivo and ex vivo are included. Introduction of compositions (e.g., nucleic acid and protein) into the cells can be carried out by methods known in the art, such as osmotic shock (e.g., calcium phosphate), electroporation, microinjection, cell fusion, etc. Introduction of nucleic acid and polypeptide in vitro, ex vivo and in vivo can also be accomplished using other techniques. For example, a polymeric substance, such as polyesters, polyamine acids, hydrogel, polyvinyl pyrrolidone, ethylene-vinylacetate, methylcellulose, carboxymethylcellulose, protamine sulfate, or lactide/glycolide copolymers, polylactide/glycolide copolymers, or ethylenevinylacetate copolymers. A nucleic acid can be entrapped in microcapsules prepared by coacervation techniques or by interfacial polymerization, for example, by the use of hydroxymethylcellulose or gelatin-microcapsules, or poly (methylmethacrolate) microcapsules, respectively, or in a colloid system. Colloidal dispersion systems include macromolecule complexes, nano-capsules, microspheres, beads, and lipid-based systems, including oil-in-water emulsions, micelles, mixed micelles, and liposomes.

Liposomes for introducing various compositions into cells are known in the art and include, for example, phosphatidylcholine, phosphatidylserine, lipofectin and DOTAP (e.g., U.S. Pat. Nos. 4,844,904, 5,000,959, 4,863,740, and 4,975,282; and GIBCO-BRL, Gaithersburg, Md.). Piperazine based amphilic cationic lipids useful for gene therapy also are known (see, e.g., U.S. Pat. No. 5,861,397). Cationic lipid systems also are known (see, e.g., U.S. Pat. No. 5,459,127). Polymeric substances, microcapsules and colloidal dispersion systems such as liposomes are collectively referred to herein as "vesicles."

Modified CPCs

In various embodiments, the present invention includes modified CPCs wherein the CPCs comprise one or more activators of Lin28a and methods of methods of use of the modified CPCs to treat or prevent a cardiac disease, disorder or injury in a subject, a tissue, or an organ in need thereof. In various embodiments, the Lin28a activator increases the amount of Lin28a polypeptide, the amount of Lin28a mRNA, the amount of Lin28a enzymatic activity, or a combination thereof. In various embodiments, the diseases and disorders where administration of a modified CPC with an increase in Lin28a activity may improve therapeutic outcome include, but are not limited to, cardiomyopathy, hypertrophic cardiomyopathy, dilated cardiomyopathy, diabetic cardiomyopathy, atherosclerosis, coronary artery disease, ischemic heart disease, myocarditis, viral infection, wounds, hypertensive heart disease, valvular disease, congenital heart disease, myocardial infarction, congestive heart failure, arrhythmias, diseases resulting in remodeling of the heart, heart failure, ischemia, myocardial infarction, transplantation, hypertension, restenosis, angina pectoris, rheumatic heart disease, injuries-physical or otherwise, or congenital cardiovascular defects.

It will be understood by one skilled in the art, based upon the disclosure provided herein, that an increase in the level of Lin28a encompasses the increase in Lin28a expression, including transcription, translation, or both. The skilled artisan will also appreciate, once armed with the teachings of the present invention, that an increase in the level of Lin28a includes an increase in Lin28a activity (e.g., enzymatic activity, substrate binding activity, etc.). Thus, increasing the level or activity of Lin28a includes, but is not limited to, increasing the amount of Lin28a polypeptide, and increasing transcription, translation, or both, of a nucleic acid encoding Lin28a; and it also includes increasing any activity of an Lin28a polypeptide as well. The Lin28a activator compositions and methods of the invention can selectively activate Lin28a or can activate both Lin28a and another molecule.

Thus, the present invention relates to the prevention and treatment of a disease or disorder by administration of a composition comprising a modified CPC comprising a Lin28a polypeptide, a recombinant Lin28a polypeptide, an active Lin28a polypeptide fragment, or an activator of Lin28a expression or activity. In one embodiment, the Lin28a polypeptide is soluble. In another embodiment, the Lin28a polypeptide is a recombinant Lin28a polypeptide.

It is understood by one skilled in the art, that an increase in the level of Lin28a encompasses an increase in the amount of Lin28a (e.g., by administration of Lin28a or a fragment thereof, by increasing Lin28a protein expression, etc.). Additionally, the skilled artisan would appreciate, that an increase in the level of Lin28a includes an increase in Lin28a activity. Thus, increasing the level or activity of Lin28a includes, but is not limited to, the administration of Lin28a or a fragment thereof, as well as increasing transcription, translation, or both, of a nucleic acid encoding Lin28a; and it also includes increasing any activity of Lin28a as well.

The increased level or activity of Lin28a can be assessed using a wide variety of methods, including those disclosed herein, as well as methods well-known in the art or to be developed in the future. That is, the routineer would appreciate, based upon the disclosure provided herein, that increasing the level or activity of Lin28a can be readily assessed using methods that assess the level of a nucleic acid encoding Lin28a (e.g., mRNA), the level of Lin28a polypeptide, and/or the level of Lin28a activity in a biological sample obtained from a subject.

One skilled in the art, based upon the disclosure provided herein, would understand that the invention is useful in subjects who, in whole (e.g., systemically) or in part (e.g., locally, tissue, organ), are being or will be, treated for bleeding. In one embodiment, the invention is useful in treating or preventing bleeding. The skilled artisan will appreciate, based upon the teachings provided herein, that the diseases and disorders treatable by the compositions and methods described herein encompass any disease or disorder where in an increase in coagulation will promote a positive therapeutic outcome.

One of skill in the art will realize that in addition to activating Lin28a directly, diminishing the amount or activity of a molecule that itself diminishes the amount or activity of Lin28a can serve to increase the amount or activity of Lin28a. Thus, an Lin28a activator can include, but should not be construed as being limited to, a chemical compound, a protein, a peptidomemetic, an antibody, a ribozyme, and an antisense nucleic acid molecule. One of skill in the art would readily appreciate, based on the disclosure provided herein, that an Lin28a activator encompasses a chemical compound that increases the level, enzymatic activity, or substrate binding activity of Lin28a. Additionally, an Lin28a activator encompasses a chemically modified compound, and derivatives, as is well known to one of skill in the chemical arts.

It will be understood by one skilled in the art, based upon the disclosure provided herein, that an increase in the level of Lin28a encompasses the increase in Lin28a expression, including transcription, translation, or both. The skilled artisan will also appreciate, once armed with the teachings of the present invention, that an increase in the level of Lin28a includes an increase in Lin28a activity (e.g., enzymatic activity, substrate binding activity, etc.). Thus, increasing the level or activity of Lin28a includes, but is not limited to, increasing the amount of Lin28a polypeptide, increasing transcription, translation, or both, of a nucleic acid encoding Lin28a; and it also includes increasing any activity of a Lin28a polypeptide as well. The Lin28a activator compositions and methods of the invention can selectively activate Lin28a, or can activate both Lin28a and another molecule. Thus, the present invention relates to administration of a modified CPC comprising a Lin28a polypeptide, a recombinant Lin28a polypeptide, an active Lin28a polypeptide fragment, or an activator of Lin28a expression or activity.

Further, one of skill in the art would, when equipped with this disclosure and the methods exemplified herein, appreciate that a Lin28a activator includes such activators as discovered in the future, as can be identified by well-known criteria in the art of pharmacology, such as the physiological results of activation of Lin28a as described in detail herein and/or as known in the art. Therefore, the present invention is not limited in any way to any particular Lin28a activator as exemplified or disclosed herein; rather, the invention encompasses those activators that would be understood by the routineer to be useful as are known in the art and as are discovered in the future.

One of skill in the art will appreciate that an activator can be administered as a small molecule chemical, a protein, a nucleic acid construct encoding a protein, or combinations thereof. Numerous vectors and other compositions and methods are well known for administering a protein or a nucleic acid construct encoding a protein to cells or tissues. Therefore, the invention includes a method of administering a protein or a nucleic acid encoding an protein that is an activator of Lin28a. (Sambrook et al., 2012, Molecular Cloning: A Laboratory Manual, Cold Spring Harbor Laboratory, New York; Ausubel et al., 1997, Current Protocols in Molecular Biology, John Wiley & Sons, New York).

One of skill in the art will realize that diminishing the amount or activity of a molecule that itself diminishes the amount or activity of Lin28a can serve to increase the amount or activity of Lin28a. Similarly, increasing the amount or activity of a molecule that itself increases the amount or activity of Lin28a can serve to increase the amount of Lin28a in a CPC of the invention. In one embodiment, a molecule that increases the amount or activity of Lin28a is a member of the miR-290 family or a homolog or ortholog thereof.

Therefore, in one embodiment, the invention relates to compositions comprising CPCs modified with a miR, pre-miR or miR mimic that increases the level or activity of Lin28a. In certain embodiments, the miR is a member of the mir-290 gene family or a homolog or ortholog thereof. In one embodiment, the miR is at least one of miR-290a, miR-291a, miR-291b, miR-292a, miR-293, miR-294, miR-295, miR-371a, miR-371b, miR-372, miR-302b or a combination thereof.

miRs are small non-coding RNA molecules that are capable of causing post-transcriptional silencing of specific genes in cells by the inhibition of translation or through degradation of the targeted mRNA. A miR can be completely complementary or can have a region of noncomplementarity with a target nucleic acid, consequently resulting in a "bulge" at the region of non-complementarity. A miR can inhibit gene expression by repressing translation, such as when the miR is not completely complementary to the target nucleic acid, or by causing target RNA degradation, which is believed to occur only when the miR binds its target with perfect complementarity. The disclosure also can include double-stranded precursors of miR. A miR can be 18-100 nucleotides in length, and more preferably from 18-80 nucleotides in length. Mature miRs can have a length of 19-30 nucleotides, preferably 21-25 nucleotides, particularly 21, 22, 23, 24, or 25 nucleotides. miR precursors typically have a length of about 70-100 nucleotides and have a hairpin conformation. miRs are generated in vivo from pre-miRs by the enzymes Dicer and Drosha, which specifically process long pre-miR into functional miR. The hairpin or mature microRNAs, or pri-microRNA agents featured in the disclosure can be synthesized in vivo by a cell-based system or in vitro by chemical synthesis. In one embodiment, a modulator of a miR is a modulator of a miR precursor, e.g. a modulator of a pre-miR.

In various embodiments, the composition comprises an oligonucleotide that contains the nucleotide sequence of at least one of miR-290a, miR-291a, miR-291b, miR-292a, miR-293, miR-294, miR-295, miR-371a, miR-371b, miR-372, miR-302b or a combination thereof. In certain embodiments, the oligonucleotide comprises the nucleotide sequence of a miR in a pre-miR, mature or hairpin form. In other embodiments, a combination of oligonucleotides comprising a sequence of one or more miRs, any pre-miR, any fragment, or any combination thereof is envisioned.

miR compositions, including, but not limited to, compositions comprising miRs, pre-miRs, miR mimics, and fragments of miRs can be synthesized to include a modification that imparts a desired characteristic. For example, the modification can improve stability, hybridization thermodynamics with a target nucleic acid, targeting to a particular tissue or cell-type, or cell permeability, e.g., by an endocytosis-dependent or -independent mechanism.

Modifications can also increase sequence specificity, and consequently decrease off-site targeting. Methods of synthesis and chemical modifications are described in greater detail below. If desired, miR compositions, including, but not limited to, compositions comprising miRs, pre-miRs, miR mimics, and fragments of miRs, may be modified to stabilize the oligonucleotide molecules against degradation, to enhance half-life, or to otherwise improve efficacy. Desirable modifications are described, for example, in U.S. Patent Publication Nos. 20070213292, 20060287260, 20060035254, 20060008822, and 2005028824, each of which is hereby incorporated by reference in its entirety. For increased nuclease resistance and/or binding affinity to the target, the single-stranded oligonucleotide agents featured in the disclosure can include 2'-O-methyl, 2'-fluorine, 2'-O-methoxyethyl, 2'-O-aminopropyl, 2'-amino, and/or phosphorothioate linkages. Inclusion of locked nucleic acids (LNA), ethylene nucleic acids (ENA), e.g., 2'-4'-ethylene-bridged nucleic acids, and certain nucleotide modifications can also increase binding affinity to the target. The inclusion of pyranose sugars in the oligonucleotide backbone can also decrease endonucleolytic cleavage. A oligonucleotide can be further modified by including a 3' cationic group, or by inverting the nucleoside at the 3'-terminus with a 3-3' linkage. In another alternative, the 3'-terminus can be blocked with an aminoalkyl group. Other 3' conjugates can inhibit 3'-5' exonucleolytic cleavage. While not being bound by theory, a 3' may inhibit exonucleolytic cleavage by sterically blocking the exonuclease from binding to the 3' end of the oligonucleotide. Even small alkyl chains, aryl groups, or heterocyclic conjugates or modified sugars (D-ribose, deoxyribose, glucose etc.) can block 3'-5'-exonucleases.

In one embodiment, the miR, pre-miR, miR mimic, or fragment includes a 2'-modified oligonucleotide containing oligodeoxynucleotide gaps with some or all internucleotide linkages modified to phosphorothioates for nuclease resistance. The presence of methylphosphonate modifications increases the affinity of the oligonucleotide for its target RNA and thus reduces the $IC_{5}Q$. This modification also increases the nuclease resistance of the modified oligonucleotide. It is understood that the methods and reagents of the present disclosure may be used in conjunction with any technologies that may be developed to enhance the stability or efficacy of an inhibitory nucleic acid molecule.

In one embodiment, miR molecules include nucleotide oligomers containing modified backbones or non-natural internucleoside linkages. Oligomers having modified backbones include those that retain a phosphorus atom in the backbone and those that do not have a phosphorus atom in the backbone. For the purposes of this disclosure, modified oligonucleotides that do not have a phosphorus atom in their internucleoside backbone are also considered to be nucleotide oligomers. Nucleotide oligomers that have modified oligonucleotide backbones include, for example, phosphorothioates, chiral phosphorothioates, phosphorodithioates, phosphotriesters, aminoalkyl-phosphotriesters, methyl and other alkyl phosphonates including 3'-alkylene phosphonates and chiral phosphonates, phosphinates, phosphoramidates, thionophosphoramidates, thionoalkylphosphonates, thionoalkylphosphotriest-ers, and boranophosphates. Various salts, mixed salts and free acid forms are also included. Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Nucleotide oligomers having modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyl eneimino and methylenehydrazino backbones; sulfonate and sulfonamide backbones; amide backbones; and others having mixed N, O, S and $CH_2$ component parts. Representative United States patents that teach the preparation of the above oligonucleotides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference. Nucleotide oligomers may also contain one or more substituted sugar moieties. Such modifications include 2'-O-methyl and 2'-methoxyethoxy modifications. Another desirable modification is 2'-dimethylaminooxyethoxy, 2'-aminopropoxy and 2'-fluoro. Similar modifications may also be made at other positions on an oligonucleotide or other nucleotide oligomer, particularly the 3' position of the sugar on the 3' terminal nucleotide. Nucleotide oligomers may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

In other nucleotide oligomers, both the sugar and the internucleoside linkage, i.e., the backbone, are replaced with groups. Methods for making and using these nucleotide oligomers are described, for example, in "Peptide Nucleic Acids (PNA): Protocols and Applications" Ed. P. E. Nielsen, Horizon Press, Norfolk, United Kingdom, 1999. Representative United States patents that teach the preparation of PNAs include, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

In other embodiments, a single stranded modified nucleic acid molecule (e.g., a nucleic acid molecule comprising a phosphorothioate backbone and 2'-OMe sugar modifications is conjugated to cholesterol.

A miR or miR mimic described herein, which may be in the pre-miR, mature or hairpin form, may be provided as a naked oligonucleotide that is capable of entering a CPC. In some cases, it may be desirable to utilize a formulation that aids in the delivery of a miR or other nucleotide oligomer to the CPCs (see, e.g., U.S. Pat. Nos. 5,656,611, 5,753,613, 5,785,992, 6,120,798, 6,221,959, 6,346,613, and 6,353,055, each of which is hereby incorporated by reference).

miR mimics can mimic the activity of a miR through inhibiting one or more genes targeted by suppressor miRNAs and consequently normalize cellular processes. Therefore, in one embodiment, the composition comprises an oligonucleotide composition that mimics the activity of a miR described herein. In certain embodiments, the composition comprises oligonucleotides having nucleobase identity to the nucleobase sequence of a miR, and are thus designed to mimic the activity of the miR. In certain embodiments, the oligonucleotide composition that mimics miR activity comprises a double-stranded RNA molecule which mimics the mature miR hairpins or processed miR duplexes. In one embodiment, a miR mimic is an LNA-modified oligonucleotide.

In one embodiment, the oligonucleotide shares identity with endogenous miR or miR precursor nucleobase sequences. An oligonucleotide selected for inclusion in a composition of the present invention may be one of a number of lengths. Such an oligonucleotide can be from 7 to 100 linked nucleosides in length. For example, an oligonucleotide sharing nucleobase identity with a miR may be from 7 to 30 linked nucleosides in length. An oligonucleotide sharing identity with a miR precursor may be up to 100 linked nucleosides in length. In certain embodiments, an oligonucleotide comprises 7 to 30 linked nucleosides. In certain embodiments, an oligonucleotide comprises 7, 8, 9, 10, 11, 12, 13, 14, 15, 16, 17, 18, 19, 20, 21, 22, 23, 24, 25, 26, 28, 29, or 30 linked nucleotides. In certain embodiments, an oligonucleotide comprises 19 to 23 linked nucleosides. In certain embodiments, an oligonucleotide is from 40 up to 50, 60, 70, 80, 90, or 100 linked nucleosides in length.

In certain embodiments, an oligonucleotide has a sequence that has a certain identity to a miR or a precursor thereof. Nucleobase sequences of mature miRs and their corresponding stem-loop sequences described herein are the sequences found in miRBase, an online searchable database of miR sequences and annotation. Entries in the miRBase Sequence database represent a predicted hairpin portion of a miR transcript (the stem-loop), with information on the location and sequence of the mature miR sequence. The miR stem-loop sequences in the database are not strictly precursor miRs, and may in some instances include the pre-miR and some flanking sequence from the presumed primary transcript. The miR nucleobase sequences described herein encompass any version of the miR, including the sequences described in Release 10.0 of the miRBase sequence database and sequences described in any earlier Release of the miRBase sequence database. A sequence database release may result in the re-naming of certain miRs. A sequence database release may result in a variation of a mature miR sequence. The compositions of the present invention encompass oligomeric compound comprising oligonucleotides having a certain identity to any nucleobase sequence version of a miRs described herein.

In certain embodiments, an oligonucleotide has a nucleobase sequence at least 60%, 65%, 70%, 75%, 80%, 85%, 90%, 95%, 97%, 98% or 99% identical to the miR over a region of 7, 8, 9, 10, 11, 12, 13, 14, 15, 16, 17, 18, 19, 20, 21, 22, 23, 24, 25, 26, 27, 28, 29, or 30 nucleobases. Accordingly, in certain embodiments the nucleobase sequence of an oligonucleotide may have one or more non-identical nucleobases with respect to the miR.

In certain embodiments, the composition comprises a nucleic acid molecule encoding a miR, precursor, mimic, or fragment thereof. For example, the composition may comprise a viral vector, plasmid, cosmid, or other expression vector suitable for expressing the miR, precursor, mimic, or fragment thereof in a desired mammalian cell or tissue.

Methods of Treatment

In one embodiment, the methods of the present invention find use in treating a patient suffering from a cardiac disease, disorder or injury. In various embodiments, a cardiac disease, disorder, or injury is one of cardiomyopathy, hypertrophic cardiomyopathy, dilated cardiomyopathy, diabetic cardiomyopathy, atherosclerosis, coronary artery disease, ischemic heart disease, myocarditis, viral infection, wounds, hypertensive heart disease, valvular disease, congenital heart disease, myocardial infarction, congestive heart failure, arrhythmias, diseases resulting in remodeling of the heart, heart failure, ischemia, myocardial infarction, transplantation, hypertension, restenosis, angina pectoris, rheumatic heart disease, injuries-physical or otherwise, or congenital cardiovascular defects.

In one embodiment, CPCs are extracted from a donor and are used to elicit a therapeutic benefit when administered to a recipient. In one embodiment, the donor and the recipient are not the same individual. Therefore in one embodiment the CPCs administered to a subject are allogeneic, syngeneic or xenogeneic CPCs to the recipient. In one embodiment, the donor and the recipient are the same individual. Therefore in one embodiment the CPCs administered to a subject are autologous CPCs.

The CPCs may be extracted in advance and stored in a cryopreserved fashion or they may be extracted at or around the time of defined need. In one embodiment, isolated CPCs of the invention can be purified and/or expanded prior to administration to a subject. As disclosed herein, the cells may be administered to the patient, or applied directly to a damaged tissue, or in proximity of a damaged tissue, without further processing or following additional procedures to further purify, modify, stimulate, or otherwise change the cells. For example, the cells obtained from a patient may be administered to a patient in need thereof without culturing the cells before administering them to the patient.

In one embodiment, the cells obtained from a patient may be cultured prior to being administered to a patient in need thereof. In one embodiment, the CPCs are cultured in vitro for at least one, at least two, at least three, at least four, at least 5, or more than 5 passages.

In one embodiment, the cells obtained from a patient may be modified prior to being administered to a patient in need thereof. In one embodiment, the treatment comprises administration of a modified CPC comprising an activator of Lin28a signaling to a subject having a cardiac disease, disorder or injury. In one embodiment, the treatment comprises administration of a modified CPC comprising one or more of miR-290a, miR-291a, miR-291b, miR-292a, miR-293, miR-294, miR-295, miR-371a, miR-371b, miR-372, miR-302b, a mimic thereof or a combination thereof to a subject identified as having a cardiac disease, disorder or injury.

In one embodiment, a therapeutic agent of the invention comprises exosomes derived from a modified CPC. In one embodiment, the treatment comprises administration of an exosome derived from a modified CPC comprising an activator of Lin28a signaling to a subject having a cardiac disease, disorder or injury. In one embodiment, the treatment comprises administration of an exosome derived from a modified CPC comprising one or more of miR-290a, miR-291a, miR-291b, miR-292a, miR-293, miR-294, miR-295, miR-371a, miR-371b, miR-372, miR-302b, a mimic thereof or a combination thereof to a subject identified as having a cardiac disease, disorder or injury.

In one embodiment, a treatment regimen may include a single administration of a composition comprising a modified CPC or an exosome derived therefrom. In another embodiment, a treatment regimen may include multiple administrations of a composition comprising a modified CPC or an exosome derived therefrom. Multiple administrations of at least one composition of the invention can occur sequentially over a period of time selected by the attending physician. Methods of assessment of treatment course are within the skill of the art of an attending physician.

A determination of the need for treatment will typically be assessed by a history and physical exam consistent with the cardiac disease, disorder or injury at issue. A subject in need of treatment according to the methods described herein will be diagnosed with a cardiac disease, disorder or injury. In one embodiment, the subject is a human. In one embodiment, the subject is an animal, including, but not limited to, mammals (e.g., horses, cows, dogs, cats, sheep, pigs, and humans), reptiles, and avians (e.g., chickens).

It should be recognized that methods of this invention can easily be practiced in conjunction with existing therapies to effectively treat or prevent disease. The methods and compositions of the invention can include concurrent or sequential treatment with non-biologic and/or biologic drugs, heart surgery, heart transplant, or any treatment appropriate for treating a cardiac disease, disorder or injury.

Modified CPCs or exosomes derived therefrom may be applied by several routes including systemic administration (e.g., intravenous injection) or by direct administration of the CPCs or exosomes to the site of intended benefit (e.g., local or topical administration). CPCs or exosomes of the invention may be administered using any known administration route, including, but not limited to local, topical, oral, subcutaneous, intravenous or intramuscular routes of administration. Cells or exosomes may be injected in a single bolus, through a slow infusion, or through a staggered series of applications separated by several hours or, provided cells are appropriately stored, several days or weeks.

In one embodiment, the route of delivery includes intravenous delivery through a standard peripheral intravenous catheter, a central venous catheter, or a pulmonary artery catheter. In one embodiment, cells are administered to the patient as an intra-vessel bolus or timed infusion. In another embodiment, CPCs or exosomes may be re-suspended in an artificial or natural medium (e.g., a hydrogel, biocompatible lattice or tissue scaffold) prior to be administered to the patient.

Dosage and Formulation

The present invention envisions treating a cardiac disease, disorder or injury in a subject by the administration of therapeutic agent, e.g. a composition comprising a modified CPC or an exosome derived therefrom.

Administration of one or more compositions of the present invention to a subject may be carried out using known procedures, at dosages and for periods of time effective to prevent or treat fibrosis in the subject. An effective amount of the one or more therapeutic compositions necessary to achieve a therapeutic effect may vary according to factors such as the state of the disease or disorder in the subject, and the age, sex, and weight of the subject. The regimen of administration may affect what constitutes an effective amount.

The dosages of the one or more compositions may be proportionally increased or decreased as indicated by the exigencies of the therapeutic situation. One of ordinary skill in the art would be able to study the relevant factors and make the determination regarding the effective amount of the therapeutic compound without undue experimentation.

Actual dosage levels of the active ingredients in the one or more pharmaceutical compositions of this invention may be varied so as to obtain an amount of the active ingredient that is effective to achieve the desired therapeutic response for a particular subject, composition, and mode of administration, without being toxic to the subject.

In particular, the selected dosage level will depend upon a variety of factors including the activity of the particular one or more compositions employed, the time of administration, the rate of excretion of the one or more compositions, the duration of the treatment, other drugs, compounds or materials used in combination with the one or more compositions, the age, sex, weight, condition, general health and prior medical history of the subject being treated, and like factors well known in the medical arts.

Administration of the therapeutic agent in accordance with the present invention may be continuous or intermittent, depending, for example, upon the recipient's physiological condition, whether the purpose of the administration is therapeutic or prophylactic, and other factors known to skilled practitioners. The administration of the modified CPC or exosome of the invention may be essentially continuous over a preselected period of time or may be in a series of spaced doses. Both local and systemic administration is contemplated. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems which are well known to the art One or more suitable unit dosage forms having the therapeutic agent(s) of the invention, which, as discussed below, may optionally be formulated for sustained release (for example using microencapsulation, see WO 94/07529, and U.S. Pat. No. 4,962,091 the disclosures of which are incorporated by reference herein), can be administered by a variety of routes including parenteral, including by intravenous and intramuscular routes. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they may be combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions, such as phosphate buffered saline solutions pH 7.0-8.0.

The agents of this invention can be formulated and administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium Ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

The active ingredients of the invention may be formulated to be suspended in a pharmaceutically acceptable composition suitable for use in mammals and in particular, in humans. Such formulations include the use of adjuvants such as muramyl dipeptide derivatives (MDP) or analogs that are described in U.S. Pat. Nos. 4,082,735; 4,082,736; 4,101,536; 4,185,089; 4,235,771; and 4,406,890. Other adjuvants, which are useful, include alum (Pierce Chemical Co.), lipid A, trehalose dimycolate and dimethyldioctadecylammonium bromide (DDA), Freund's adjuvant, and IL-12. Other components may include a polyoxypropylene-polyoxyethylene block polymer (Pluronic®), a non-ionic surfactant, and a metabolizable oil such as squalene (U.S. Pat. No. 4,606,918).

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

Accordingly, the pharmaceutical composition of the present invention may be delivered via various routes and to various sites in a mammal body to achieve a particular effect (see, e.g., Rosenfeld et al., 1991; Rosenfeld et al., 1991a; Jaffe et al., supra; Berkner, supra). One skilled in the art will recognize that although more than one route can be used for administration, a particular route can provide a more immediate and more effective reaction than another route. Local or systemic delivery can be accomplished by administration comprising application or instillation of the formulation into body cavities or by parenteral introduction, comprising intramuscular, intravenous, peritoneal, subcutaneous, intradermal, as well as topical administration.

The active ingredients of the present invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and mammal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the pharmaceutical composition in the particular host.

These methods described herein are by no means all-inclusive, and further methods to suit the specific application will be apparent to the ordinary skilled artisan. Moreover, the effective amount of the compositions can be further approximated through analogy to compounds known to exert the desired effect.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Example 1: MicroRNAs and Cardiac Repair

Figure 2:
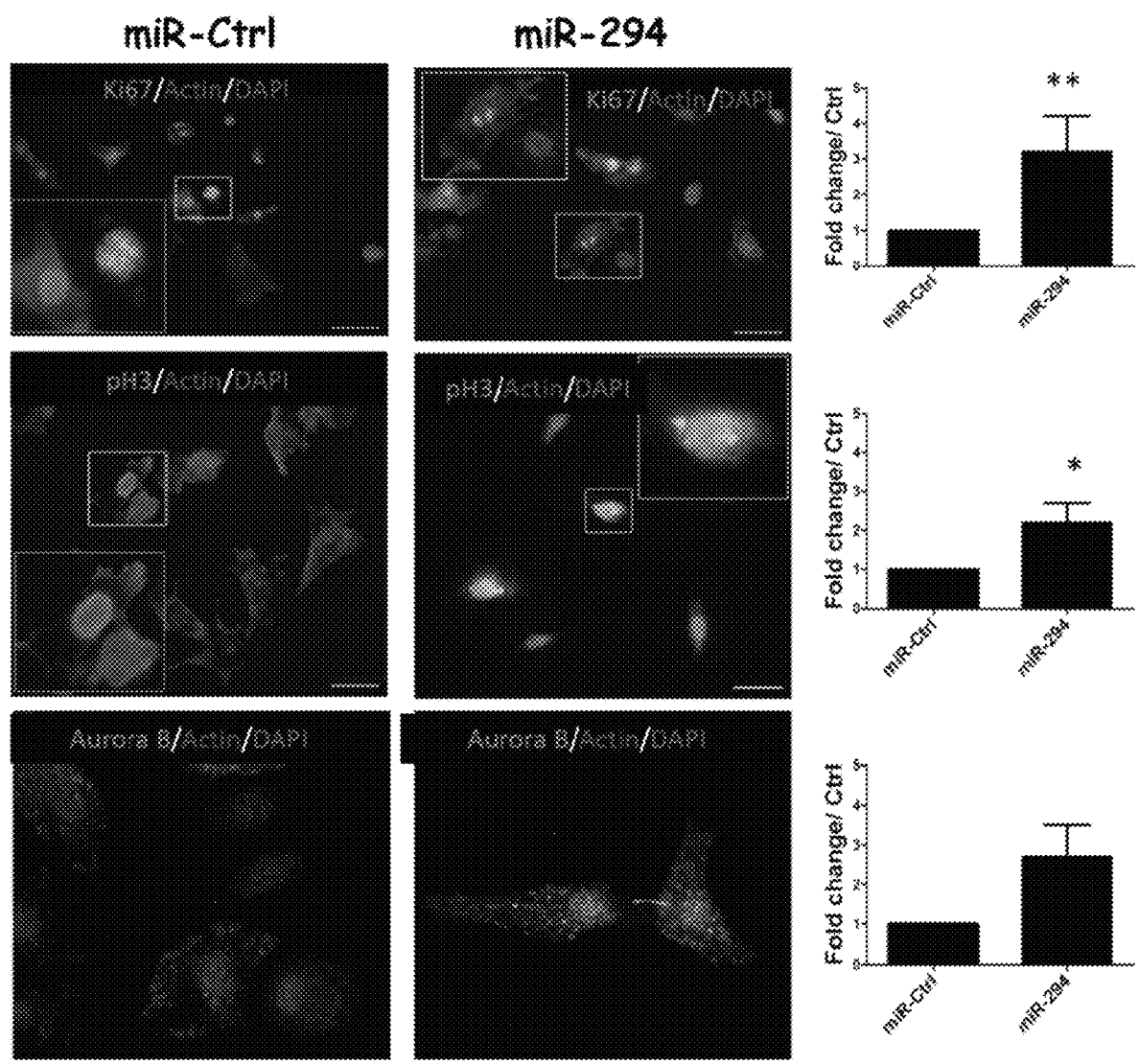
FIG. 2 depicts the results of exemplary experiments demonstrating neonatal rat cardiomyocytes (NRCMs) showed increased Ki67 and aurora B expression after treatment with miR-294
Figure 3:
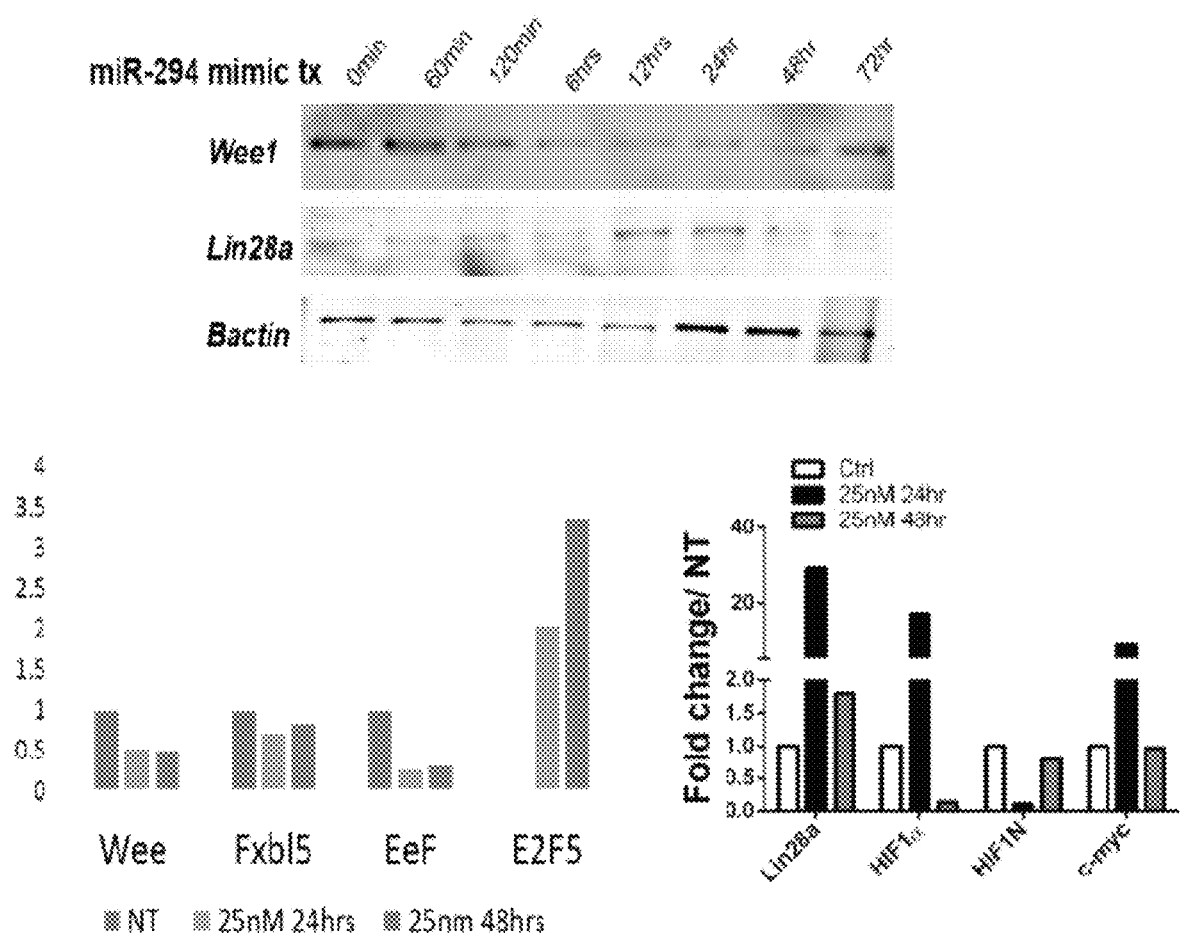
FIG. 3 depicts the results of exemplary experiments demonstrating that the underlying mechanism of action of miR-294 was tied to targeting of Wee1 and Lin28a both at the mRNA and protein level as well as Fxbl5, eEF and E2F5.
Figure 4:
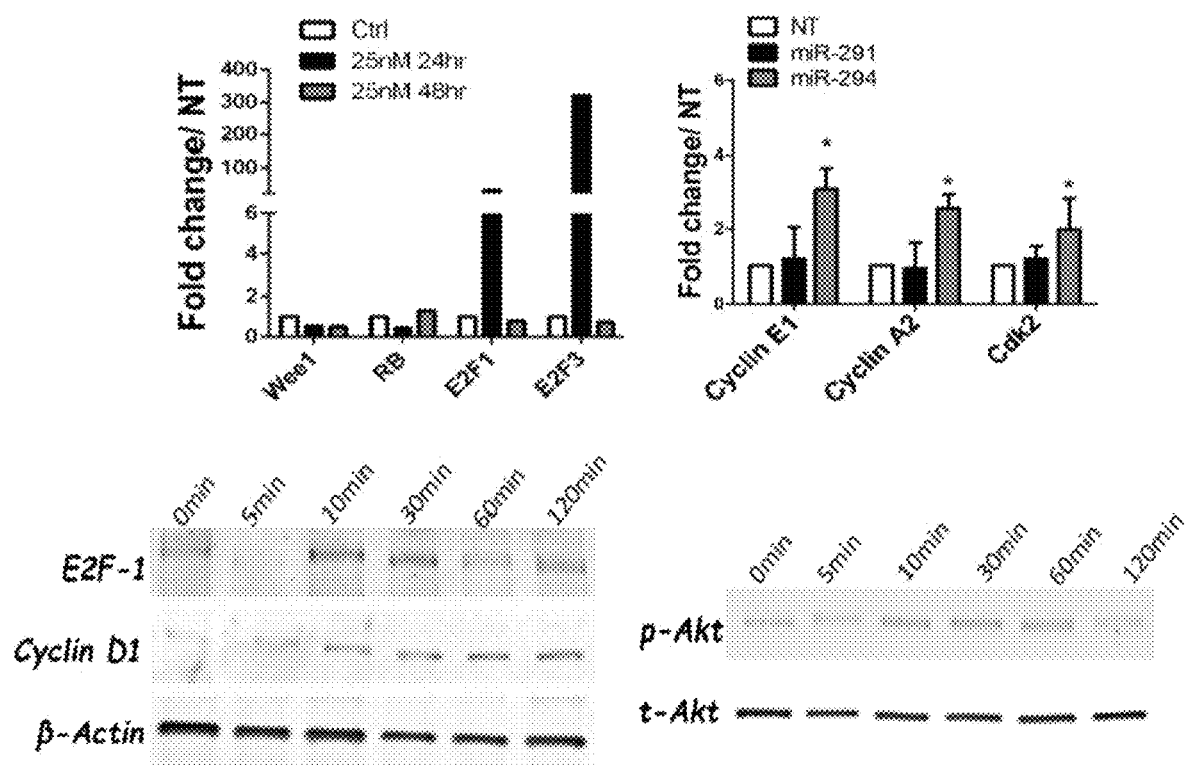
FIG. 4 depicts the results of exemplary experiments demonstrating that cell cycle markers (Cyclin E1, A2, Cdk2, E2F1, E2F3) were increased and cell cycle inhibitors (Wee1, Rb) were inhibited upon treatment with miR-294.

Over the years, microRNAs (miRNA) have emerged as important regulators of cardiac development and function (FIG. 2). Expression of various miRNA families directly correspond to physiological and pathological changes in the cardiac milieu (Chen et al., Proc Natl Acad Sci USA. 2008; 105:2111-2116; Rao et al., Circ Res. 2009; 105:585-594) while their loss or impairment is associated with development of cardiomyopathies and heart failure (Thum et al., Circulation. 2007; 116:258-267; van Rooij et al., Proc Natl Acad Sci USA. 2006; 103:18255-18260). The developmental heart is characterized by high cardiomyocyte turnover that is lost with adulthood (Porrello et al., Science. 2011; 331:1078-1080). The miRNA signature in the adult heart undergoes a dramatic shift and expression of many proprolferative miRs, characteristic of the developmental stages that are either lost or altered (Chen and Wang, J Mol Cell Cardiol. 2012; 52:949-957; Tian et al., Sci Transl Med. 2015; 7:279ra238). Recent approaches using miRNA therapeutics establish their importance for tissue replenishment in the heart after pathological challenge (Chen and Wang, J Mol Cell Cardiol. 2012; 52:949-957; Tian et al., Sci Transl Med. 2015; 7:279ra238; Porrello et al., Proc Natl Acad Sci USA. 2013; 110:187-192). Moreover, CPC functional characteristics such as proliferation, survival and cardiomyogenic commitment are highly dependent on miRNA expression (Hosoda et al., Circulation. 2011; 123:1287-1296; Sluijter et al., Arterioscler Thromb Vasc Biol. 2010; 30:859-868; Sirish et al., J Mol Cell Cardiol. 2012; 52:264-272). The present invention is partly directed to delivery of embryonic miRNAs in the heart as a novel therapy for reactivation of dormant cardiac repair processes. Recent studies have identified that the salutary effects of embryonic stem cell (ESCs) derived exosomes are dependent on delivery of embryonic stem cell cycle (ESCC) miR-290 family and in particular miR-294 (Khan et al., Circ Res. 2015; 117:52-64). This family of miRNAs, comprising at least 14 members, carries the common seed sequence "AAGUGCU" and forms 70% of the entire miRNA content in embryonic stem cells (Landgraf et al., Cell. 2007; 129:1401-1414). Some of the key ESC properties such as pluripotency (Wang et al., Nat Genet. 2008; 40:1478-1483), self-renewal (Lichner et al., Differentiation. 2011; 81:11-24), differentiation (Zovoilis et al., Differentiation. 2009; 78:69-78) and more recently the "specialized pluripotent cell metabolism" (Cao et al., EMBO J. 2015; 34:609-623) are under the direct control of miR-290 family including miR-294. Further, miR-290 family has been shown to regulate activity of key metabolic enzymes linking metabolism to pluripotency (Cao et al., EMBO J. 2015; 34:609-623). Nevertheless, the role of miR-294 in the context of the heart and CPC function has never been studied before.

miR-294 Augments CPC Proliferation and Cell Cycle miR-294 constitute 70% of the entire microRNA content in the ESCs and regulates characteristic ESC properties such as proliferation (Landgraf et al., Cell. 2007; 129:1401-1414) and cell cycle (Wang et al., Nat Genet. 2008; 40:1478-1483). CPCs in the developmental stages have increased proliferation, therefore, without being bound by a particular theory, it was hypothesized that reintroduction of miR-294 will activate developmental signaling pathways leading to enhanced CPC proliferation and cell cycle progression. For this purpose microRNA lentivirus based approaches were used for expression of miR-294 in CPCs. CPCs were derived from mouse hearts and then lentivirally engineered to express miR-294 together with a GFP tag (CPCemiR) while GFP expressing CPCs (CPCe) were used as controls. CPC overexpressing miR-294 showed increased proliferation, cell number, ATP content and metabolic activity (FIG. 1) together with decreased doubling time compared to control CPCs (FIG. 1).

miR-294 Promotes Cell Cycle Reentry and Molecular Proliferative Signaling in Cardiomyocytes Studies conducted recently show that cardiomyocytes during development proliferate rapidly yet undergo cell cycle arrest in the adult heart (Porrello et al., Science. 2011; 331:1078-1080). A number of different strategies have been employed to promote cell cycle reentry in cardiomyocytes including the use of microRNAs (Chen and Wang, J Mol Cell Cardiol. 2012; 52:949-957; Tian et al., Sci Transl Med. 2015; 7:279ra238). Since miR-294 is highly expressed during developing embryo, without being bound by a particular theory, it is hypothesized that it may have a role in cardiomyocyte proliferation. Therefore, effect of miR-294 on cardiomyocyte cell cycle and molecular proliferative signaling was assessed. Neonatal rat cardiomyocytes (NRCMs) showed increased Ki67 (FIG. 2) and aurora B (FIG. 2) expression after treatment with miR-294. Underlying mechanism was tied to targeting of Wee1 and Lin28a both at the mRNA and protein level (FIG. 3) as well as Fxbl5, eEF and E2F5 (FIG. 3). Moreover, manipulation of downstream targets such as HIF, HIF1N, c-myc (FIG. 3) was also observed together with increased cell cycle markers (Cyclin E1, A2, Cdk2, E2F1, E2F3; FIG. 4) and inhibition of cell cycle inhibitors (Wee1, Rb; FIG. 4) at the mRNA and protein level (FIG. 3) in NRCMs treated with miR-294. AKT phosphorylation was also significantly increased in NRCMs treated with miR-294 compared to controls (FIG. 4). In order to determine whether miR-294 can also influence adult cardiomyocyte proliferation, adult feline cardiomyocytes (AFM), ideally suited for long term cell culture conditions were used. AFM treated with miR-294 showed increased p-histone-3+ cells (FIG. 5) and significant upregulation of miR-294 expression and cell cycle markers (Cyclin D1, E1. B1 and CDK1) (FIG. 5) measured by quantitative RT-PCR.

Figure 6:
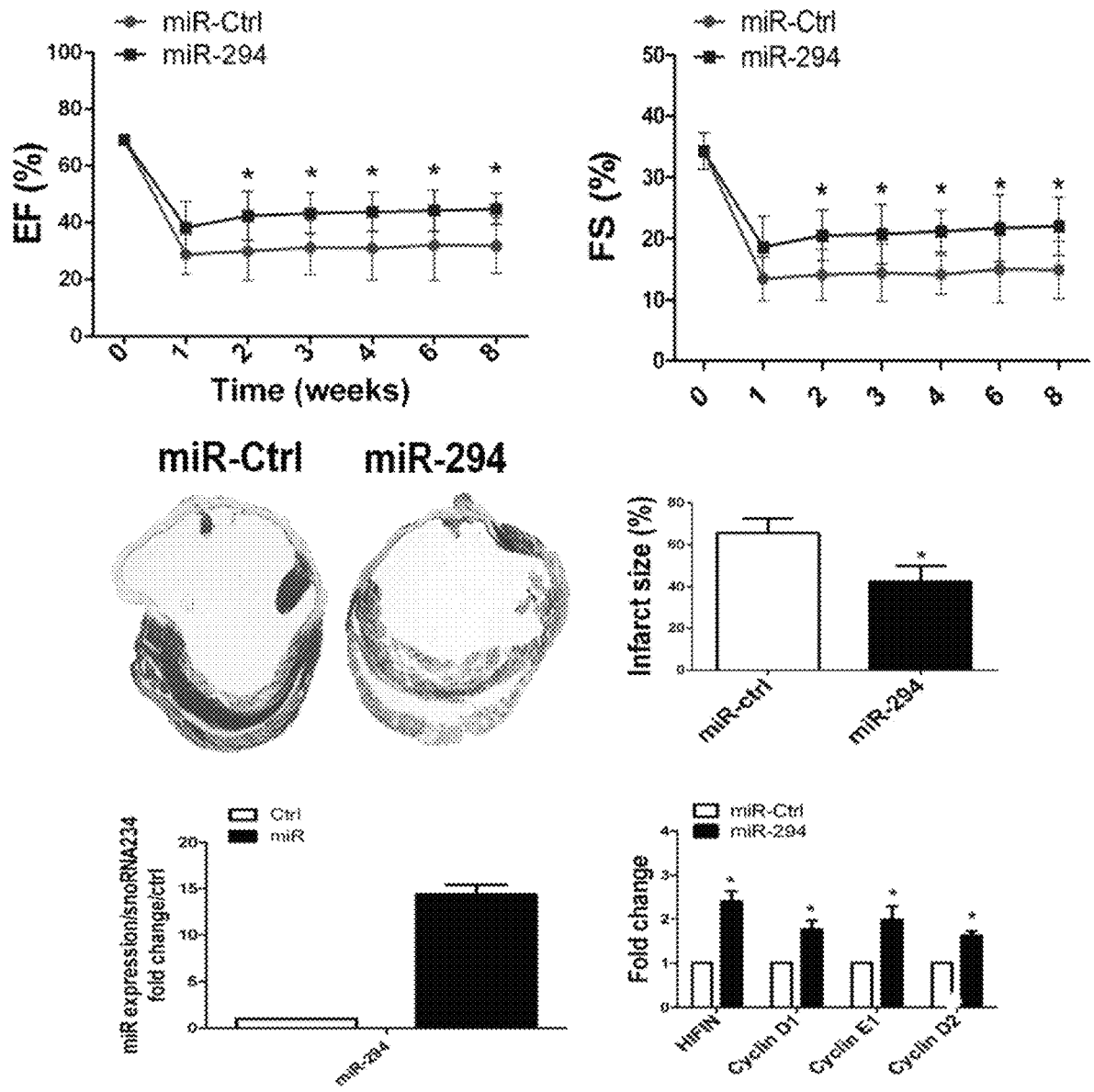
FIG. 6 depicts the results of exemplary experiments demonstrating that there was increased ejection fraction and fractional shortening (FS) along with reduced infarct size in miR-294 administered animals compared to miR-control animals. Animals with miR-294 administration showed increase mRNA levels of the miR showing successful delivery and increased expression of signaling targets of the miR-294 (HIF1N, Cyclin D1, E1, D2) compared to control miRNA injected animals.

Cardiac Therapeutic Efficacy of miR-294 Delivery in the Heart after Myocardial Infarction Studies with LNA-miR-294 systemically delivered to a small cohort of mice subjected to myocardial infarction showed increased ejection fraction (EF; FIG. 6) and fractional shortening (FS; FIG. 6) along with reduced infarct size (FIG. 6) in miR-294 administered animals compared to miR-control animals. Animals with miR-294 administration showed increase mRNA levels of the miR showing successful delivery (FIG. 6) and increased expression of signaling targets of the miR-294 (HIF1N, Cyclin D1, E1, D2) (FIG. 6) compared to control miRNA injected animals.

Figure 7:
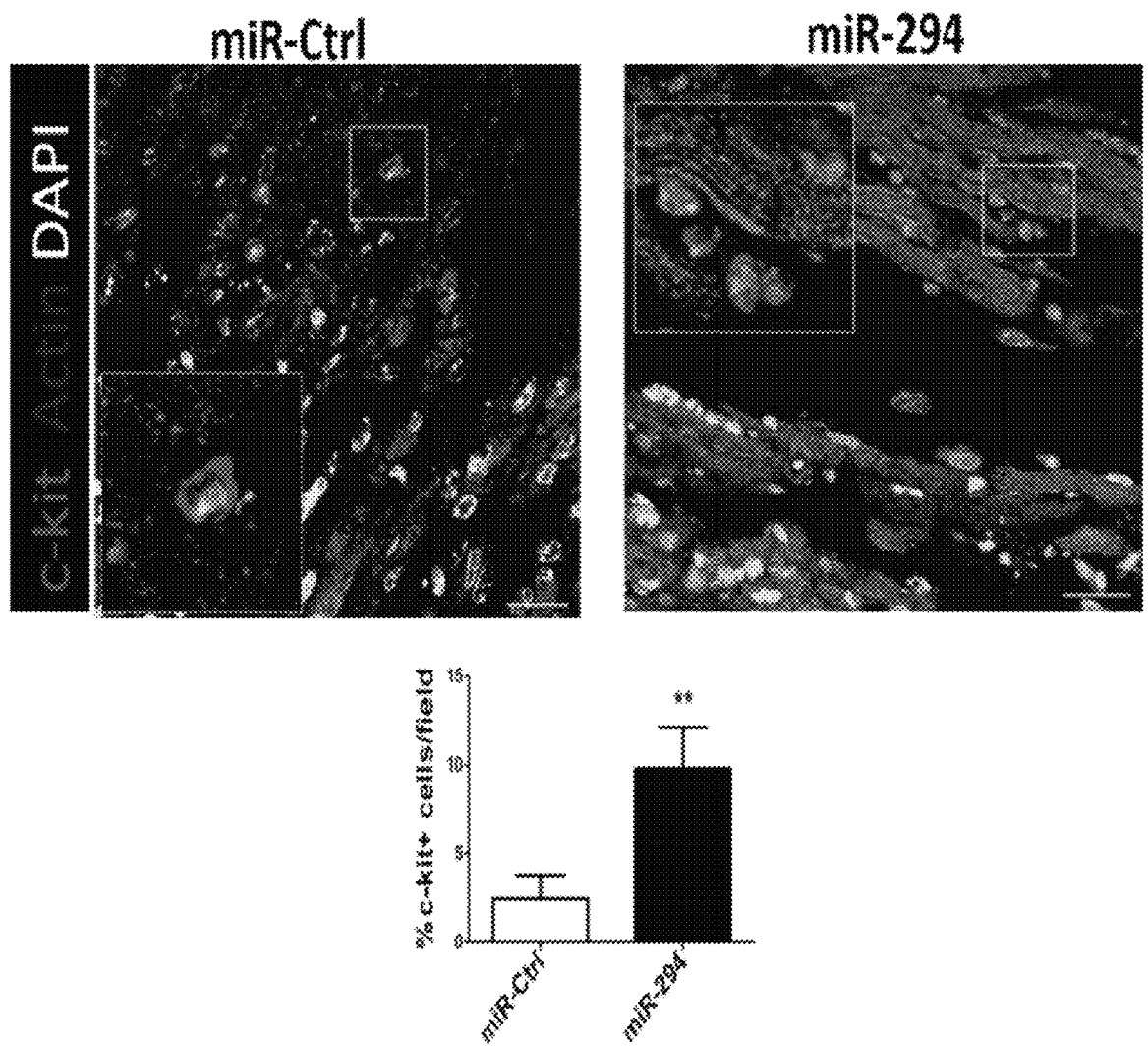
FIG. 7 depicts the results of exemplary experiments demonstrating that histological assessment revealed augmentation of c-kit+ CPCs in the heart 5 days after myocardial infarction.
Figure 8:
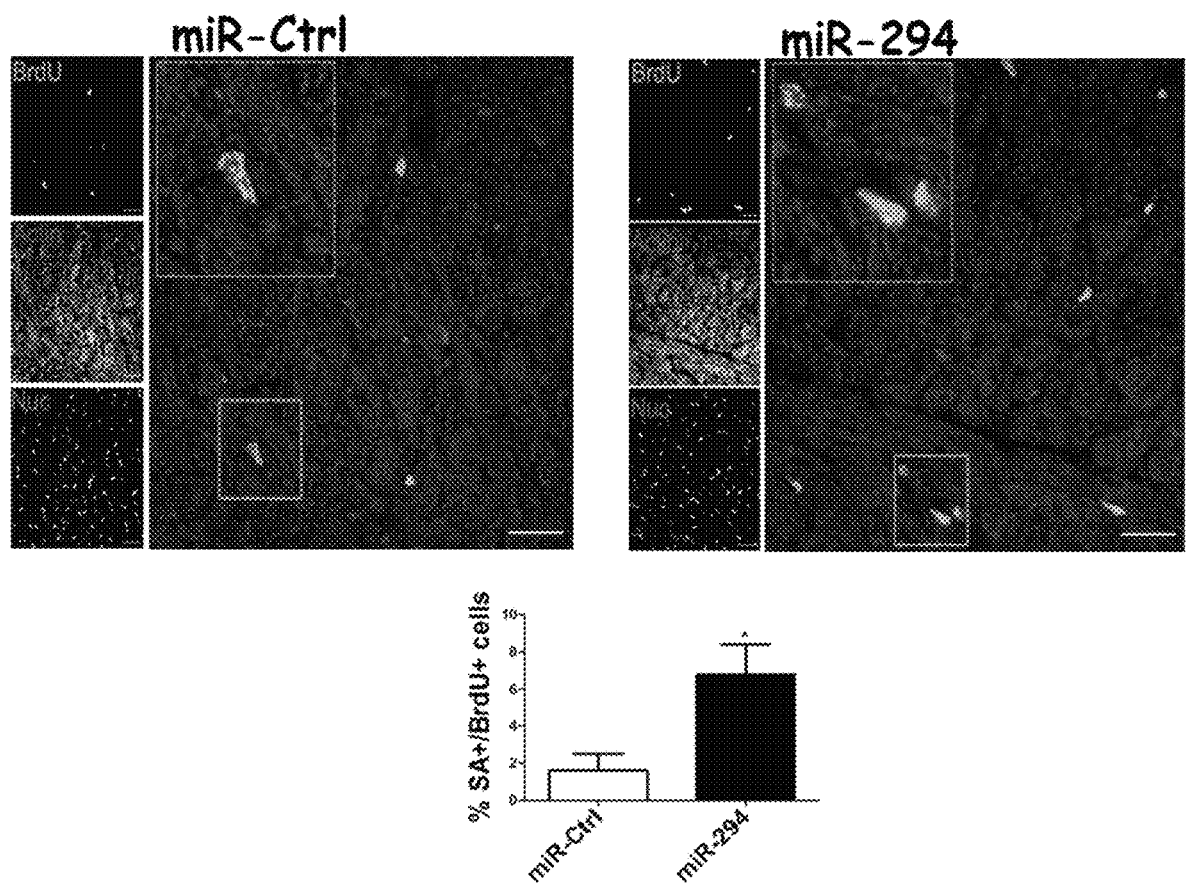
FIG. 8 depicts the results of exemplary experiments demonstrating that: histological assessment revealed an increase in the number of BrdU+ cardiomyocytes.
Figure 9:
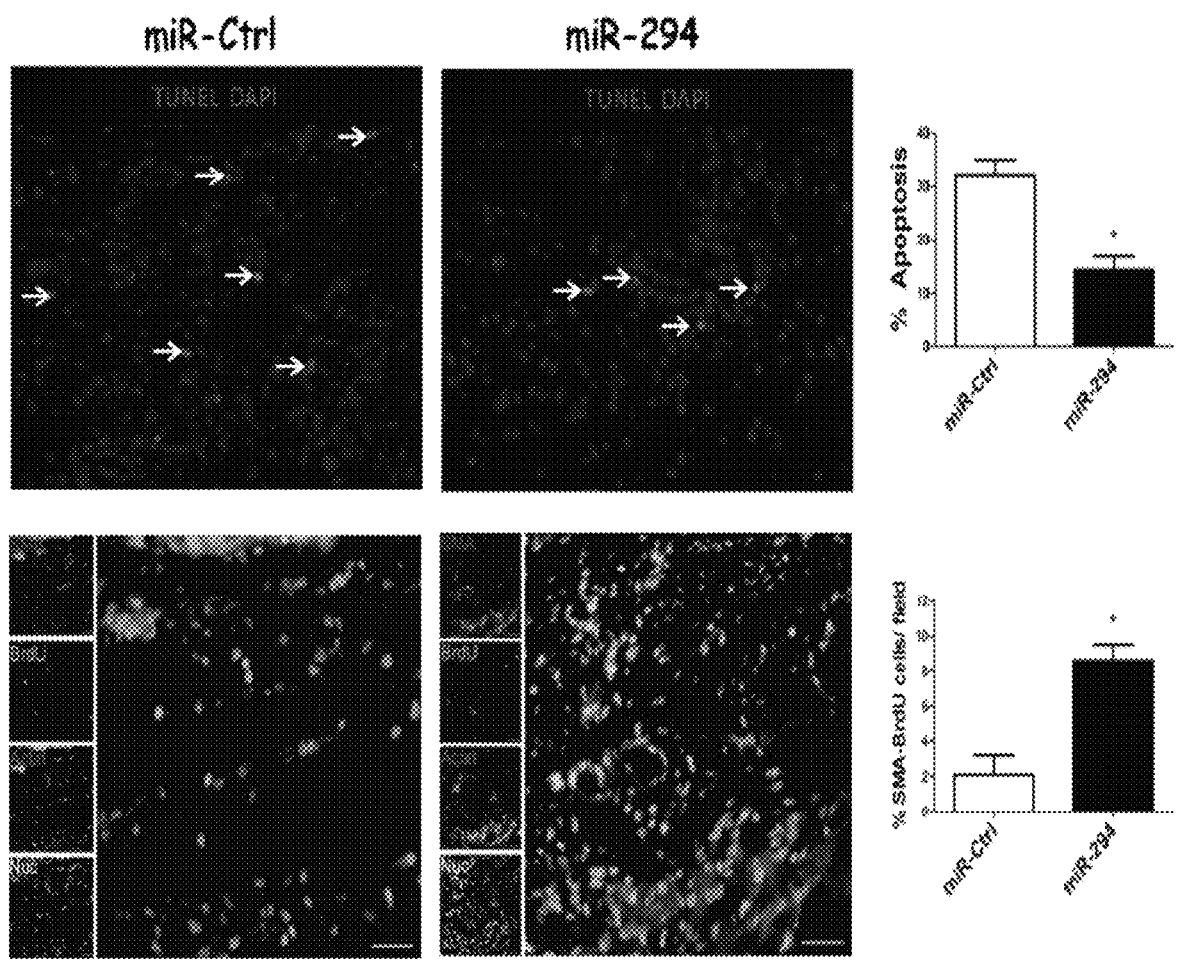
FIG. 9 depicts the results of exemplary experiments demonstrating that an analysis of neovascularization showed increased SMA+/BrdU+ cells in the hearts of animals receiving miR-294 compared to control animals.

Histological assessment revealed augmentation of c-kit+ CPCs in the heart 5 days after myocardial infarction (FIG. 7) along with increase in the number of BrdU+ cardiomyocytes (FIG. 8). Analysis of apoptosis demonstrated decreased number of TUNEL+ nuclei in the miR-294 hearts (FIG. 9). Analysis of neovascularization showed increased SMA+/BrdU+ cells in the hearts receiving miR-294 compared to control animals (FIG. 9).

Transgenic Inducible Overexpression of miR-294

Figure 10:
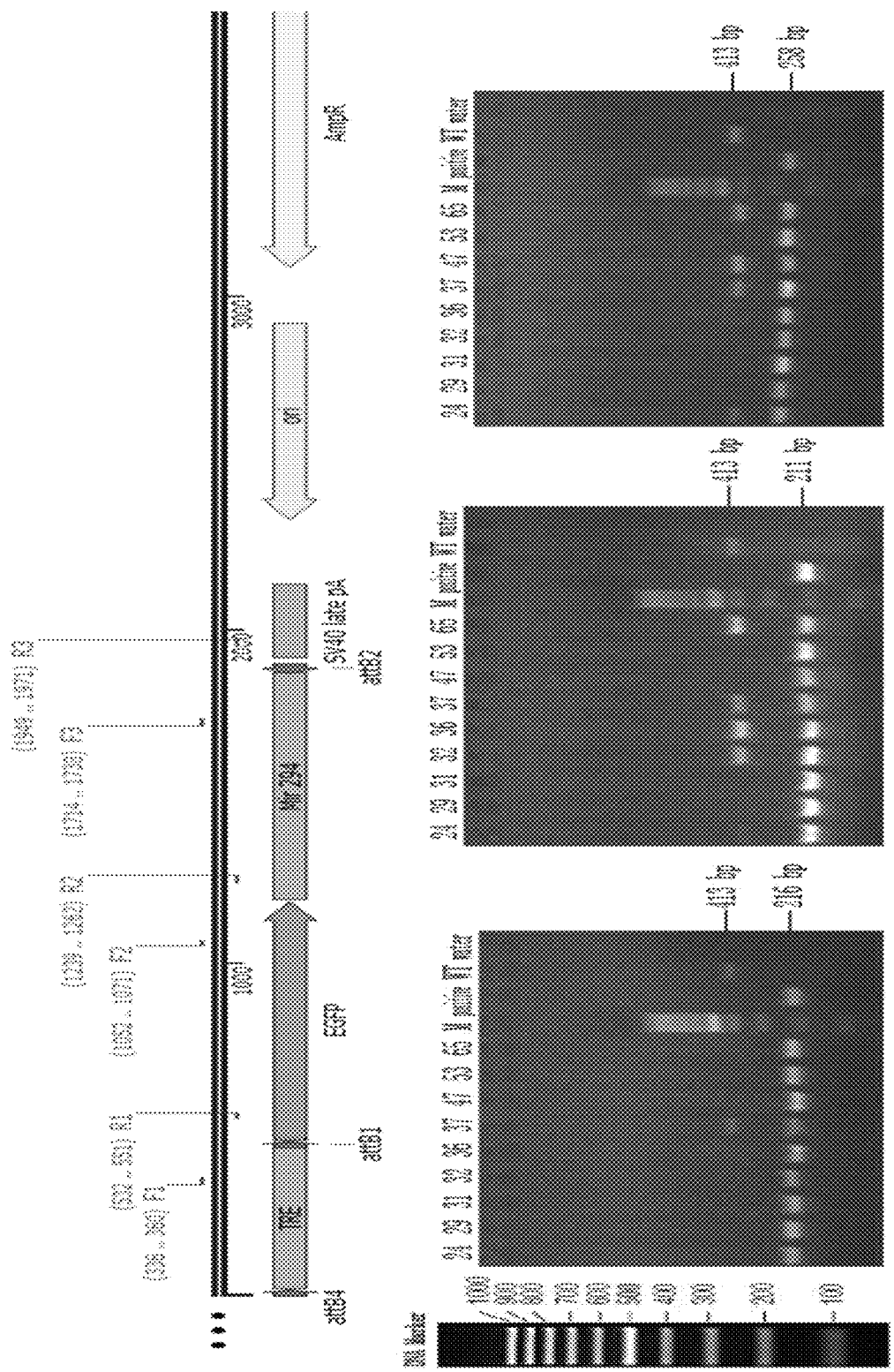
FIG. 10 depicts the results of exemplary experiments demonstrating the genotype validation of tet-inducible-miR-294 transgenic mice by qRT-PCR.

In order to determine the effect of miR-294 expression on the heart, a novel mouse model was created for miR-294 overexpression under the control of tet-promoter along with enhanced green fluorescence (EGFP) induction (FIG. 10). Confirmation of transgene was done by quantitative RT-PCR analysis.

Example 2: Lin28a—Regulator of Survival, Proliferation and Bioenergetics

Lin28a is a bona fide downstream target of miR-294 (Melton et al., Nature. 2010; 463:621-626; Hanina et al., PLoS Genet. 2010; 6:e1001163) and critical for growth and metabolism of pluripotent stem cells (Gruber et al., Nucleic Acids Res. 2014; 42:9313-9326). Lin28a expression is lost in adult tissues during development while its reintroduction leads to reprogramming cellular bioenergetics into a juvenile state thereby enhancing organ repair and regeneration (Shyh-Chang et al., Cell. 2013 Nov. 7; 155(4):778-92; Shyh-Chang and Daley, Cell Stem Cell. 2013 Apr. 4; 12(4): 395-406). Lin28a is known to bind and increase translation of several key metabolic enzymes and target mRNAs for growth and survival (Shyh-Chang et al., Cell. 2013 Nov. 7; 155(4):778-92; Peng et al., Stem Cells. 2011 March; 29(3): 496-504). In the cardiac context, emerging data suggests a cardioprotective role for Lin28a against ischemic injury (Zhang et al., PLoS One. 2014 Oct. 14; 9(10):e1 10580). Nevertheless, there is no report showing effect of Lin28a on CPC function even though other stem cells in their fetal states are associated with high Lin28a expression mediating corresponding effects on proliferation and self-renewal (Yuan et al., Science. 2012 Mar. 9; 335(6073):1195-200). Further, regenerative properties are lost in adult CPCs (Torella et al., Circ Res. 2004; 94:514-524; Frati et al., Curr Pharm Des. 2011; 17:3252-3257), meriting the need to explore whether Lin28a reintroduction in adult CPCs from the human heart leads to enhancement of their function and repair potential. CPCs from the human heart display heterogeneous growth and repair properties due their origin in patients with different cardiac disease pathologies (Mohsin et al., Circ Res. 2013 Oct. 25; 113(10):1169-79). Consequently, ex vivo propagation of human CPCs or use of their cell-free agents such as exosomes for cardiac therapy may not be a viable option since the parent cells have limited cardiac repair. Alternatively, Lin28a modification of human CPCs allows a strategy to restore lost repair potential due to age and disease thereby increasing CPC therapeutic value post transplantation including ability to secrete "cardioprotective exosomes" at the site of injury.

Figure 11:
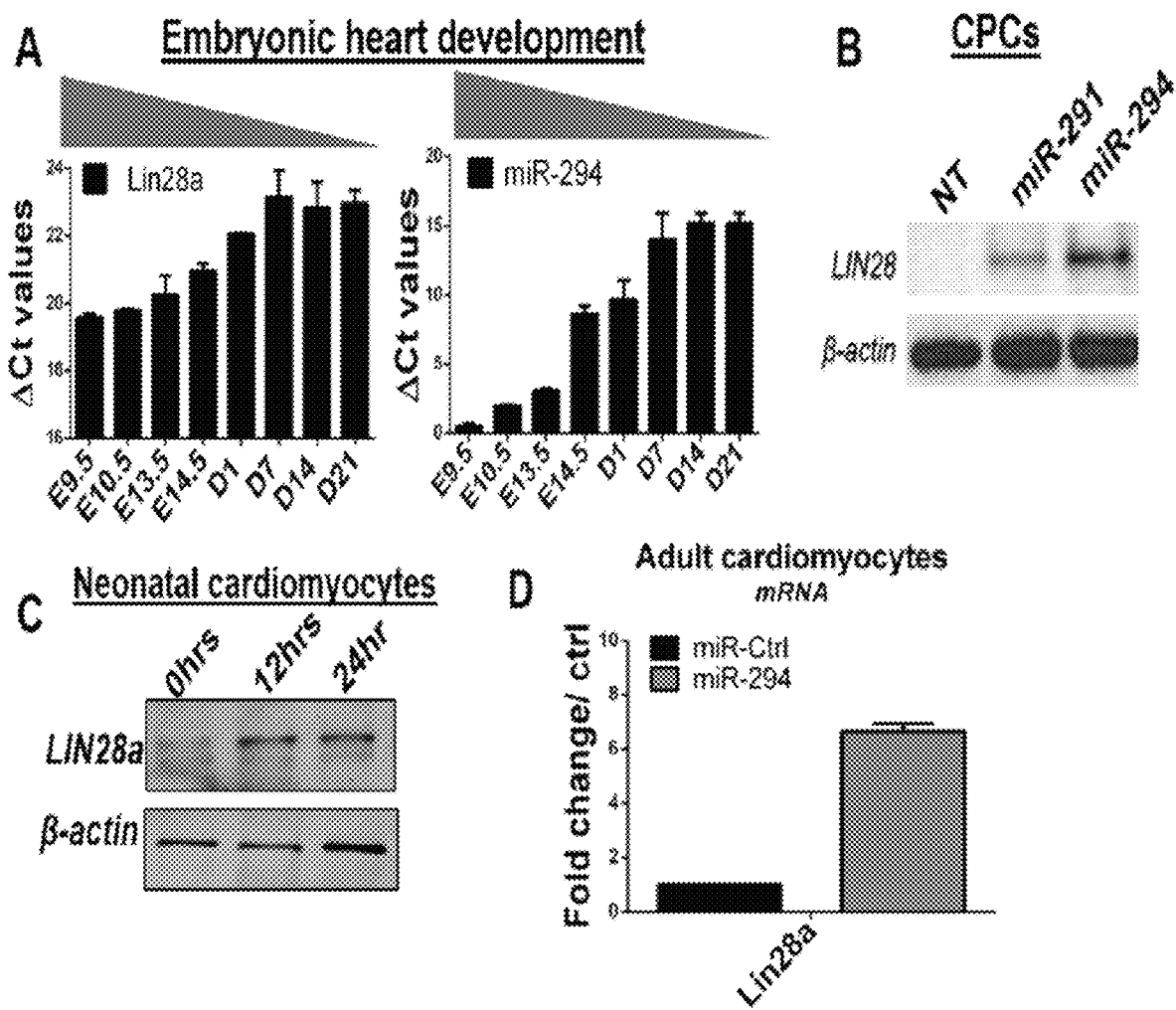
FIG. 11 depicts the results of exemplary experiments demonstrating that miR-294 and Lin28a mRNA expression coincides during embryonic heart development and declines rapidly after birth with complete abrogation in the 3 week old adult heart.

MiR-294 and Lin28a are Expressed in the Heart During Development miR-294 and Lin28a are both expressed in the developing embryo and are critical for maintenance of embryonic stem cell function (Melton et al., Nature. 2010; 463:621-626; Hanina et al., PLoS Genet. 2010; 6:e1001163; Gruber et al., Nucleic Acids Res. 2014; 42:9313-9326). Nevertheless, there is no evidence regarding the role of both miR-294 and Lin28a in the cardiac context. Our preliminary findings show that miR-294 and Lin28a mRNA expression coincides during embryonic heart development and declines rapidly after birth with complete abrogation in the 3 week old adult heart (FIG. 11).

miR-294 Drives Lin28a Expression in CPCs.

Figure 12:
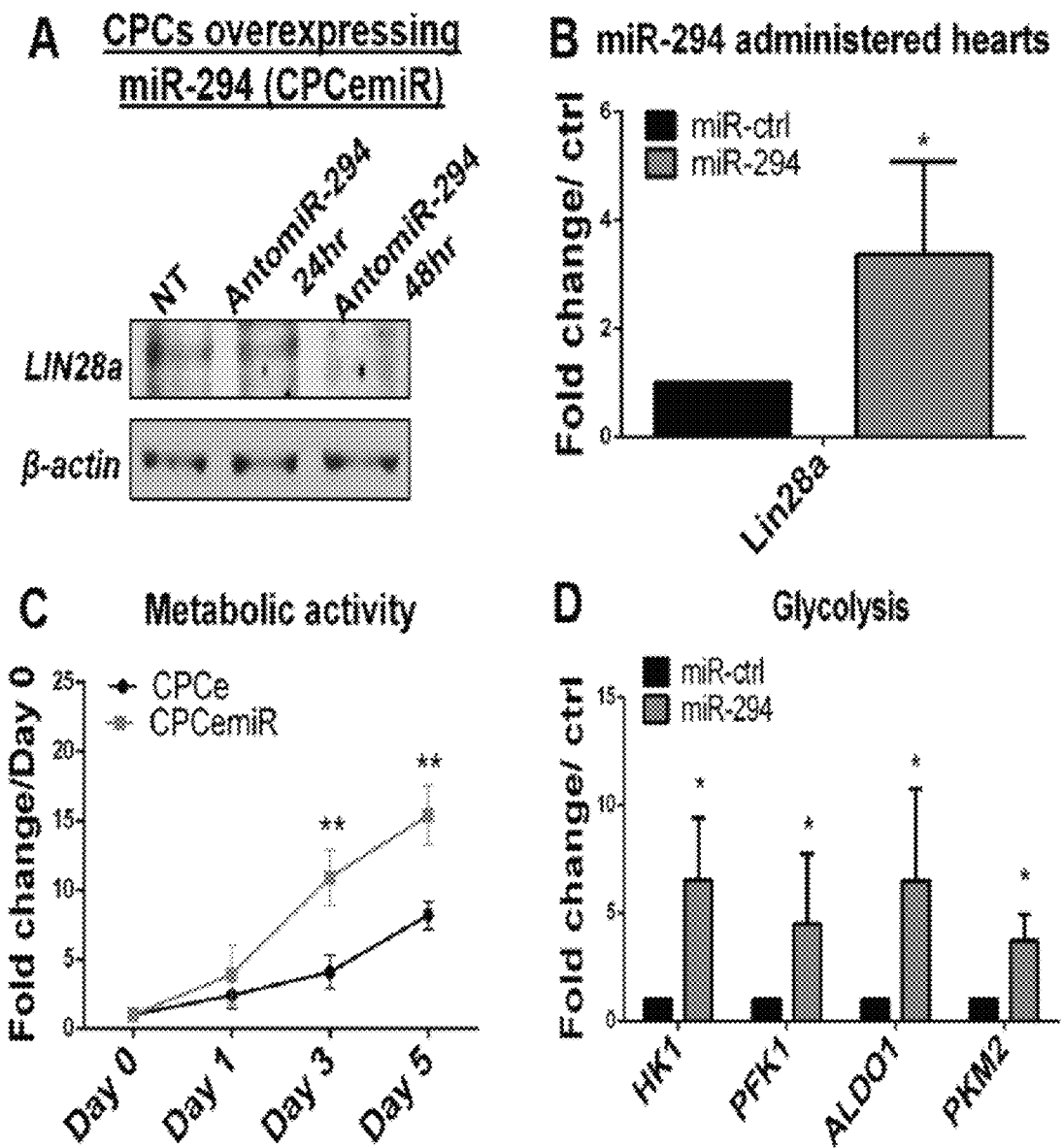
FIG. 12 depicts the results of exemplary experiments demonstrating that miR-294 administered animals showed increased mRNA levels of Lin28a in the heart compared to control animals demonstrating that miR-294 drives Lin28a expression.

Studies with ESCs have established that miR-294 maintenance of core ESC characteristics is tied to upregulation of Lin28a expression (Melton et al., Nature. 2010; 463:621-626; Hanina et al., PLoS Genet. 2010; 6:e1001163). Therefore, the ability of miR-294 treatment in CPC to enhance Lin28a expression was determined and a significant increase in Lin28a protein expression was observed (FIG. 11). Concurrently, NRCMs showed a similar increase in Lin28a protein levels (FIG. 11) parallel with enhanced mRNA level in adult cardiomyocytes after miR-294 treatment (FIG. 11). To further validate miR-294-Lin28a correlation, CPCs genetically modified to overexpress miR-294 (CPCemiR) were treated with a miR-294 antagomiR. Lin28a protein expression showed significant increase in CPCemiR but decreased after treatment with the antagomiR in CPCemiR (FIG. 12). Similarly, miR-294 administered animals showed increased mRNA levels of Lin28a in the heart compared to control animals (FIG. 12) demonstrating that miR-294 drives Lin28a expression.

Lin28a Reintroduction in CPCs Augments Bioenergetics.

Figure 13:
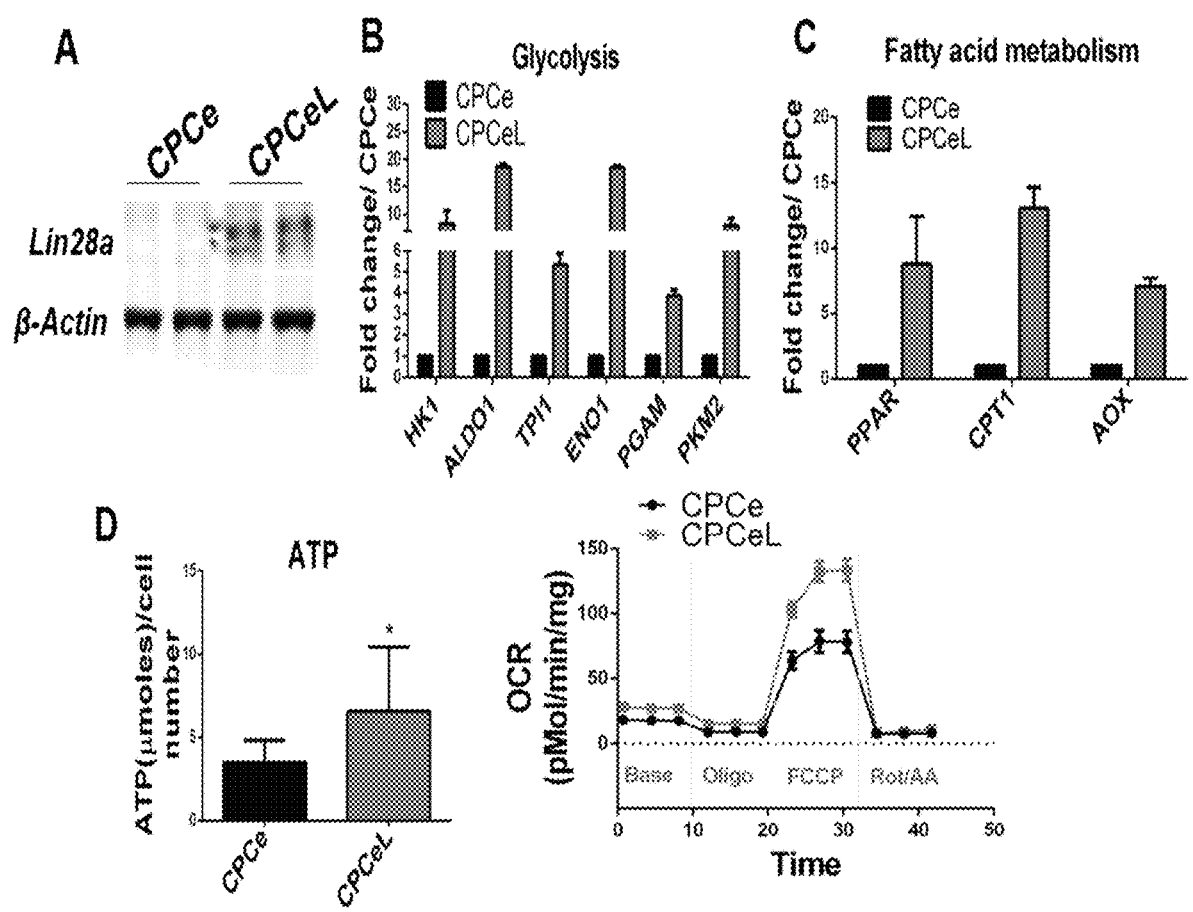
FIG. 13 depicts the results of exemplary experiments demonstrating that CPCs were lentivirally engineered to express Lin28a tagged with GFP (CPCeL) confirmed by immunoblot analysis (FIG. 3) while GFP engineered CPC (CPCe) were used as controls.

Recent studies indicate that Lin28a reintroduction in adult tissue enhances repair and regeneration through reconfiguration of cellular bioenergetics (Shyh-Chang et al., Cell. 2013 Nov. 7; 155(4):778-92). The findings presented herein show increased metabolic activity (FIG. 12) in CPCemiR compared to CPCs engineered with GFP (CPCe) together with elevated mRNA levels of glycolytic enzymes (HK1, PFK1, ALDO1 and PKM2) (FIG. 12) concurrent with Lin28a upregulation as shown in FIG. 11. Whether enhanced metabolic features in the miR-294 CPCs are dependent on Lin28a since Lin28a with reconfiguration of cellular bioenergetics will be tested in the next set of experiments. CPCs were lentivirally engineered to express Lin28a tagged with GFP (CPCeL) confirmed by immunoblot analysis (FIG. 13) while GFP engineered CPC (CPCe) were used as controls. Assessment of metabolic enzymes in CPCeL showed significant increase in mRNA levels of glycolytic (HK1, ALDO1, TPI1, ENO1, PGAM, PKM2) (FIG. 13) and fatty acid oxidation enzymes (PPAR, CPT1, AOX) (FIG. 13) compared to control cells. In parallel, increased intracellular ATP levels (FIG. 13) were observed in Lin28a CPCs compared to GFP expressing control CPCs (CPCe) indicating higher bioenergetics of Lin28a CPCs. Analysis of mitochondrial oxidative phosphorylation (OxPhos) demonstrated significant increase of maximal respiration in Lin28a CPCs measured by Seahorse assay compared to control CPCs (FIG. 3) indicating bioenergetic CPC morphology after Lin28a modification.

Bioenergetic Lin28a CPCs Display Improved Survival and Proliferation.

Figure 14:
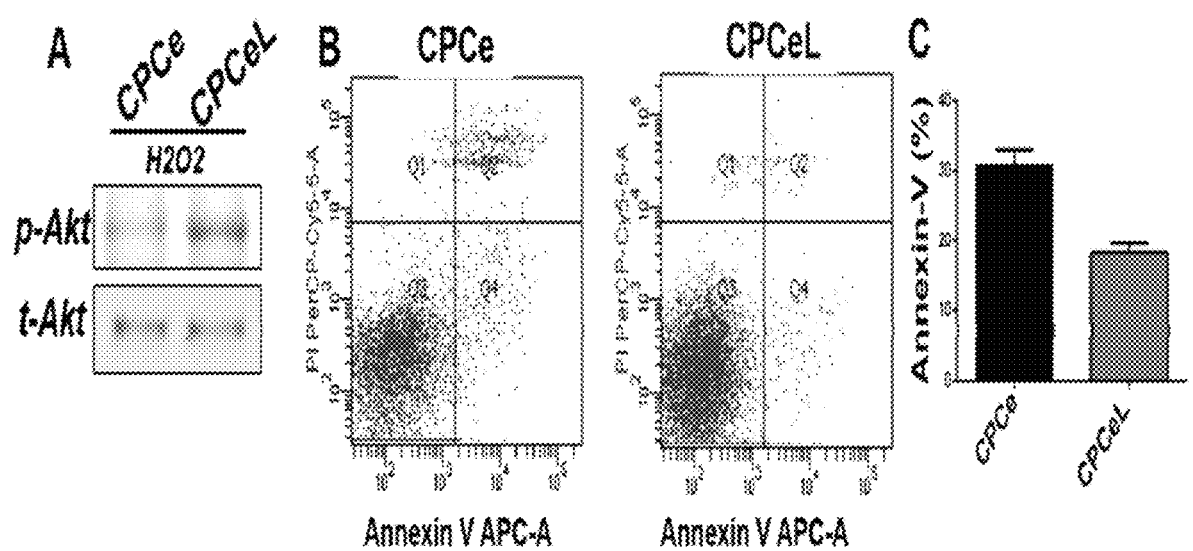
FIG. 14 depicts the results of exemplary experiments demonstrating that CPCeL showed significant increase in AKT phosphorylation in response $H_2O_2$ challenge compared to CPCe, together with a decrease in Annexin-V+, as measured by FACS.

The next set of experiments was designed to determine whether Lin28a modification increased core CPC function. CPCeL showed significant increase in AKT phosphorylation in response H2O2 challenge compared to CPCe (FIG. 14) together with decrease Annexin-V+ cells as measured by FACS (FIG. 14). Additionally, Collectively, Lin28a enhances CPC bioenergetic state that in turn leads to augmentation of CPCs response to stress.

Lin28a Overexpression in Human CPCs Enhanced Exosome Function.

Figure 5:
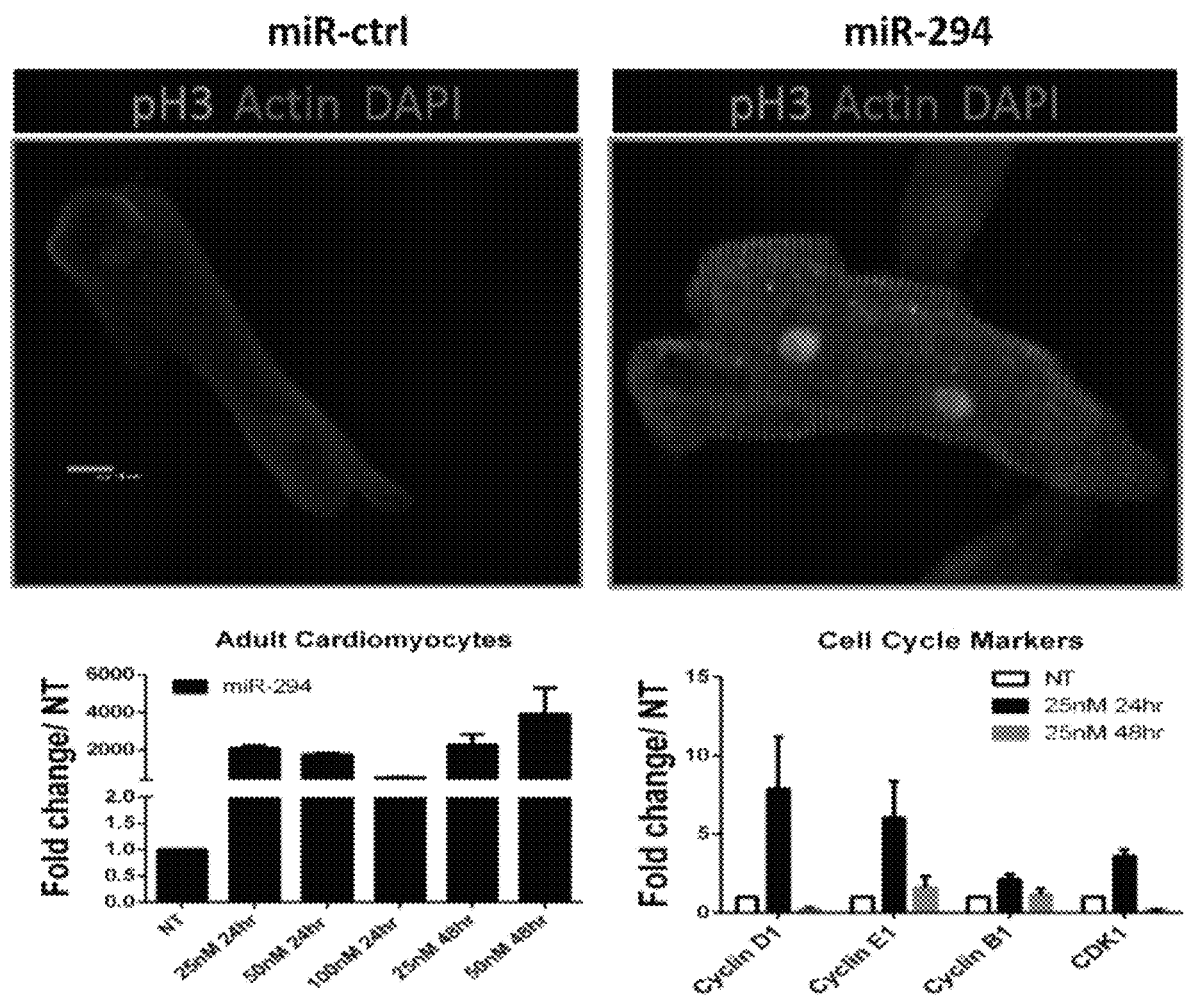
FIG. 5 depicts the results of exemplary experiments demonstrating that AFM treated with miR-294 showed increased p-histone-3+ cells and significant upregulation of miR-294 expression and cell cycle markers (Cyclin D1, E1. B1 and CDK1).
Figure 15:
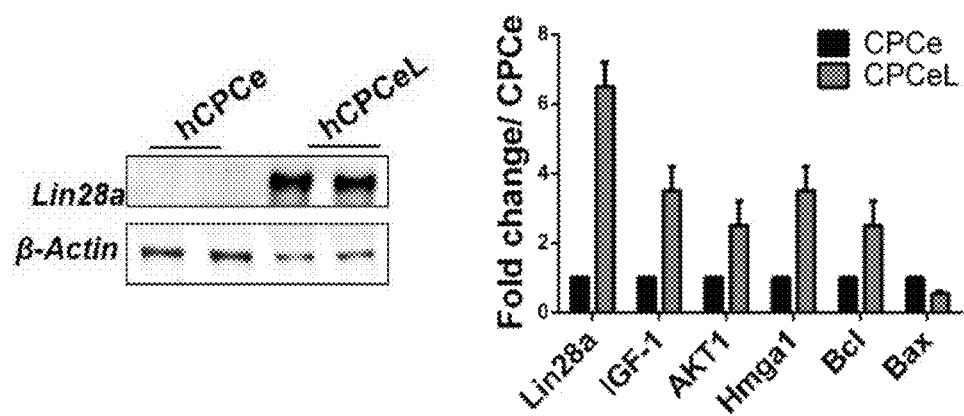
FIG. 15 depicts the results of exemplary experiments demonstrating that human CPCs lentivirally engineered to overexpress Lin28a tagged with GFP showed. increased expression of Lin28a and survival genes (IGF-1, AKT1, Hmga1, Bcl-2) and decreased Bak mRNA expression.

In order to test the therapeutic potential of Lin28a, human CPCs were isolated from cardiac tissue of heart failure patients undergoing left ventricular assist device implantation. Human CPCs were lentivirally engineered to overexpress Lin28a tagged with GFP (FIG. 15). Increased expression of Lin28a and survival genes (IGF-1, AKT1, Hmga1, Bcl-2) and decreased Bak mRNA expression (FIG. 5).

Example 3: Pluripotent Stem Cell MicroRNA-294 as a Mediator of Cardiac Proliferative Response in the Heart after Myocardial Infarction The embryonic heart is composed of rapidly dividing cardiomyocytes that give rise to a working myocardium. Cardiomyocytes retain some proliferative capacity in neonates but lose most of it in adulthood. Embryonic stem cell cycle (ESCC) miRs are a class of microRNAs regulating the unique cell cycle of ESCs and their characteristic pluripotency. Nevertheless, expression of miR-294, a member of the ESCC miRs is lost during developmental transitions from the ESCs to mature cells. The effect of miR-294 to induce cardiac proliferation and heart function has not been previously studied.

The data presented herein demonstrates that the miR-290 family, including miR-294, drives cardiomyocyte/CPC cell cycle leading to augmentation of cardiac function after myocardial infarction.

Figures 16A, 16B:
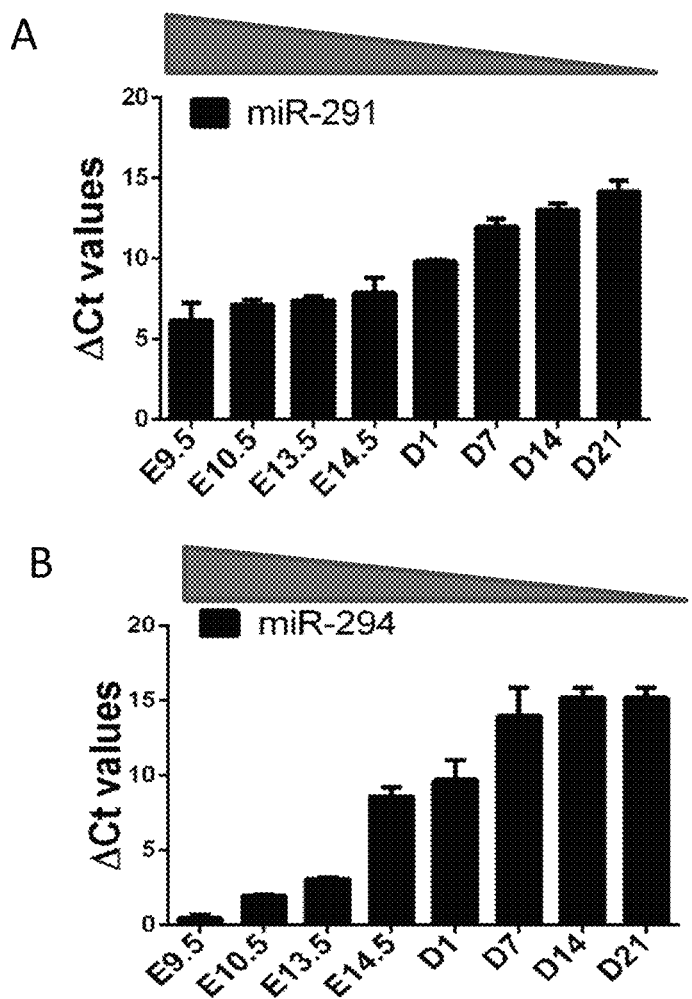
FIG. 16A through FIG. 16B, depicts the results of exemplary experiments demonstrating miR expression in the heart during development.
Figures 17A, 17B, 17C, 17D, 17E, 17F:
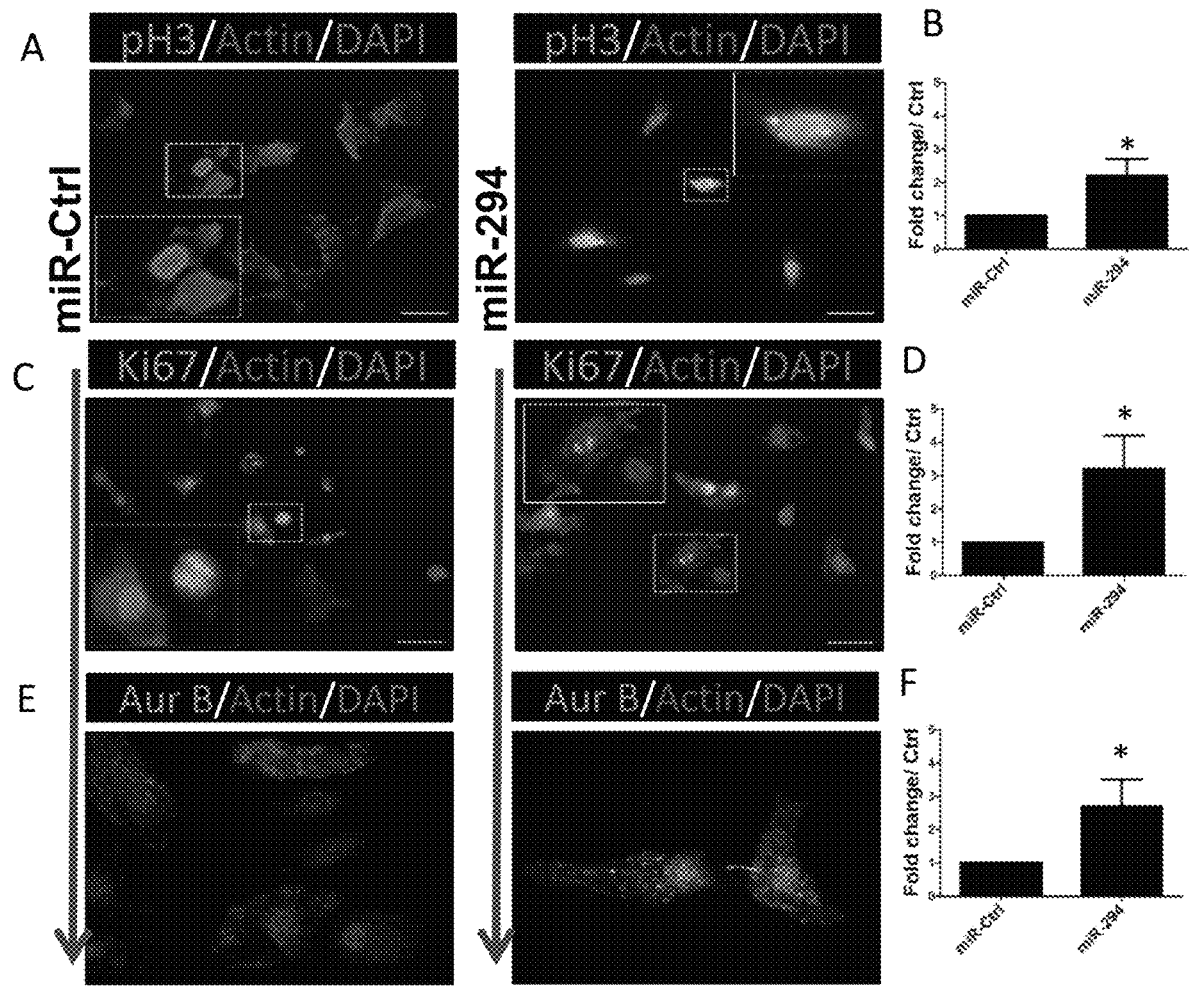
FIG. 17A through FIG. 17F, depicts the results of exemplary experiments demonstrating miR-294 treatment increases cell cycle markers in neonatal rat cardiomyocytes (NRCMs).

The experimental methods and results are now described:

An analysis of miR expression in the heart during development revealed elevated levels of miR-294 in the prenatal stages while the expression was lost in the neonates and adults as confirmed by qRT-PCR (FIG. 16). Neonatal ventricular cardiomyocytes (NRVMs) were treated with miR-294 mimic to determine the effect on proliferation and cell cycle. Elevated mRNA levels of cyclins A2, E1, CDK2 together with E2F1 and E2F3 was observed in NRVMs treated with 25 nM mimic for miR-294 (FIG. 17). Additionally, miR-294 treated NRVMs showed in AKT phosphorylation along with enhanced protein levels of cyclin D1 and E2F1. Increased expression of p-histone 3, Ki67 and Aurora B kinase (G2/M) was confirmed by immunocytochemistry in NRVMs after miR-294 treatment compared to control cells. Similarly, CPCs treated with miR-294 mimic and a lentivirus for miR-294 showed increased cell cycle progression, survival and expression of Lin28 and PDK-4 (FIG. 17).

Figures 18A, 18B, 18C:
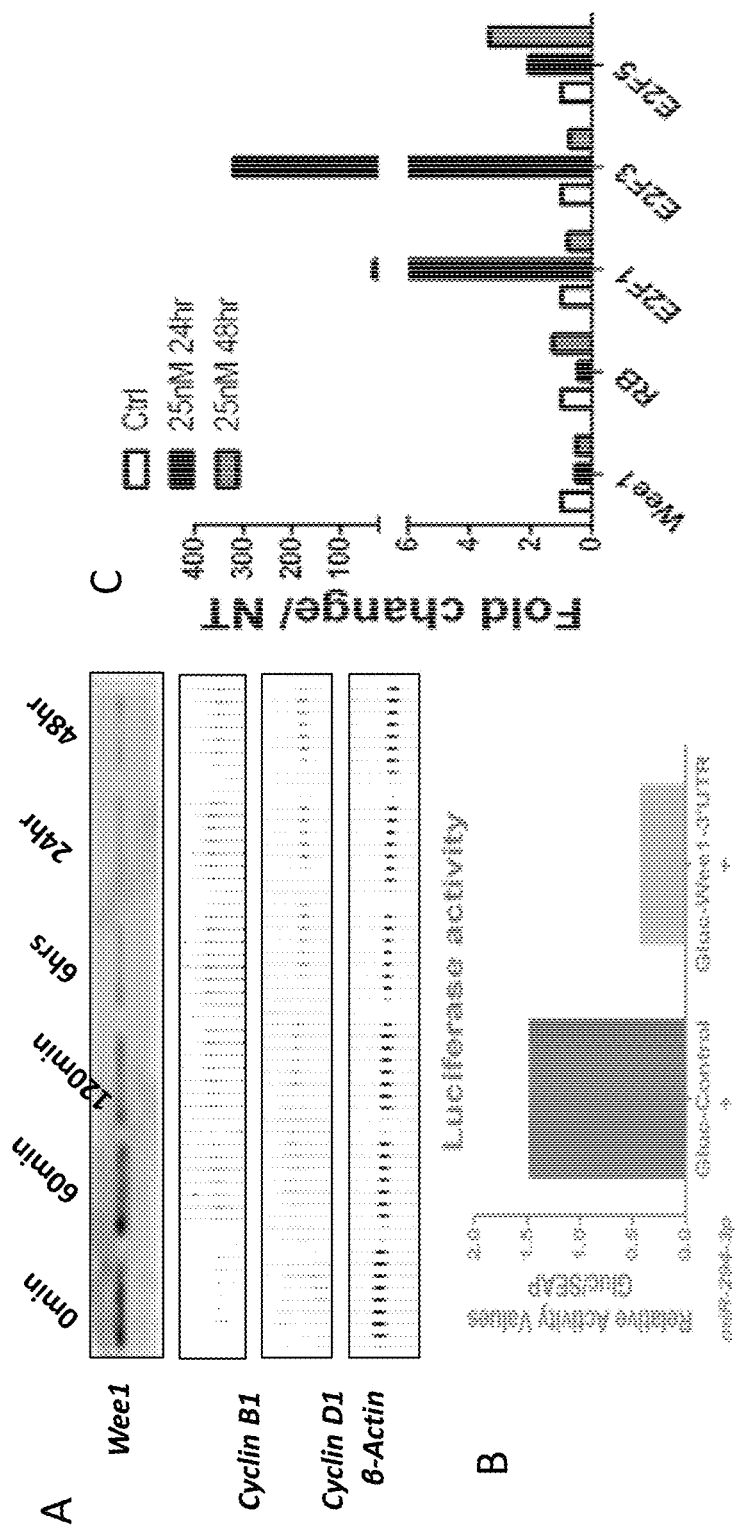
FIG. 18A through FIG. 18C, depicts the results of exemplary experiments demonstrating miR-294 modulates cell cycle markers in neonatal rat cardiomyocytes.
Figures 19A, 19B, 19C:
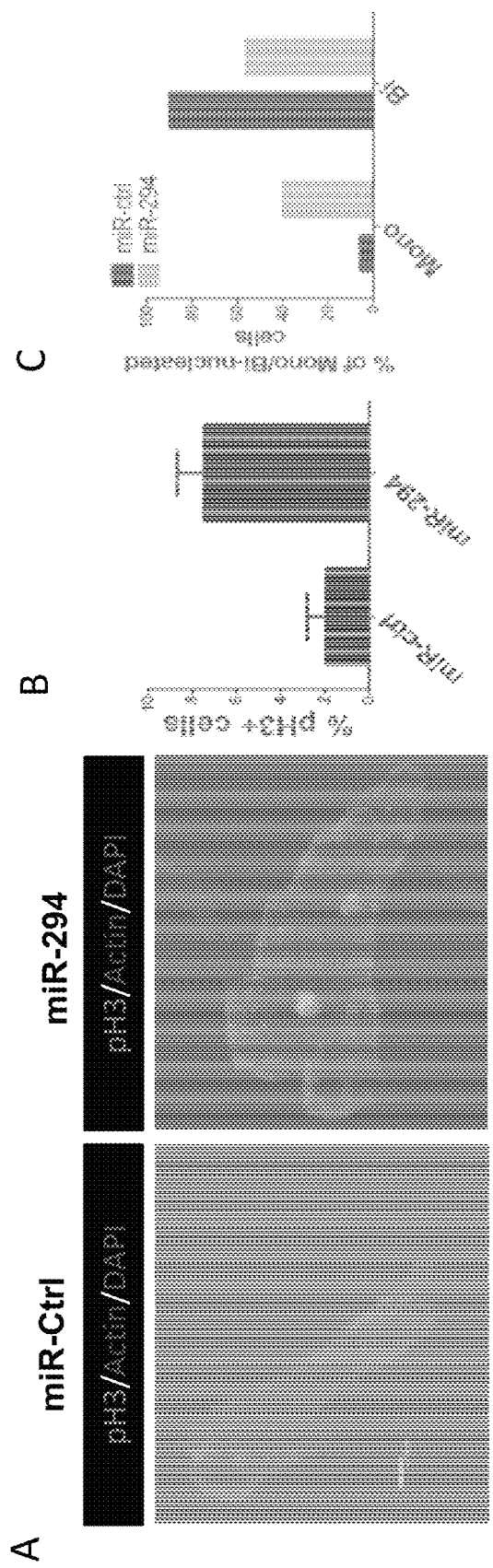
FIG. 19A through FIG. 19C, depicts the results of exemplary experiments demonstrating adult feline cardiomyocytes treated with miR-294 show increased cell cycle activity.
Figures 20A, 20B, 20C, 20D, 20E, 20F, 20G:
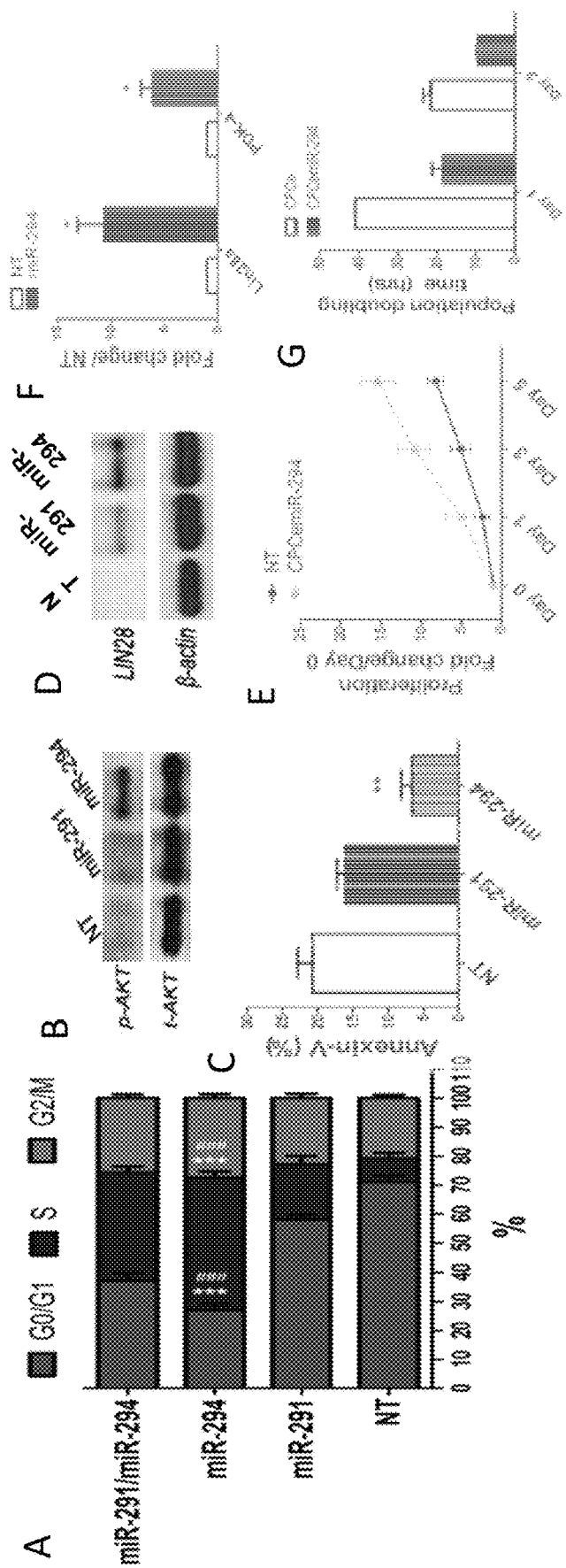
FIG. 20A through FIG. 20G, depicts the results of exemplary experiments demonstrating that cardiac progenitor cells have enhanced proliferation and survival after miR-294 treatment.
Figures 21A, 21B, 21C, 21D:
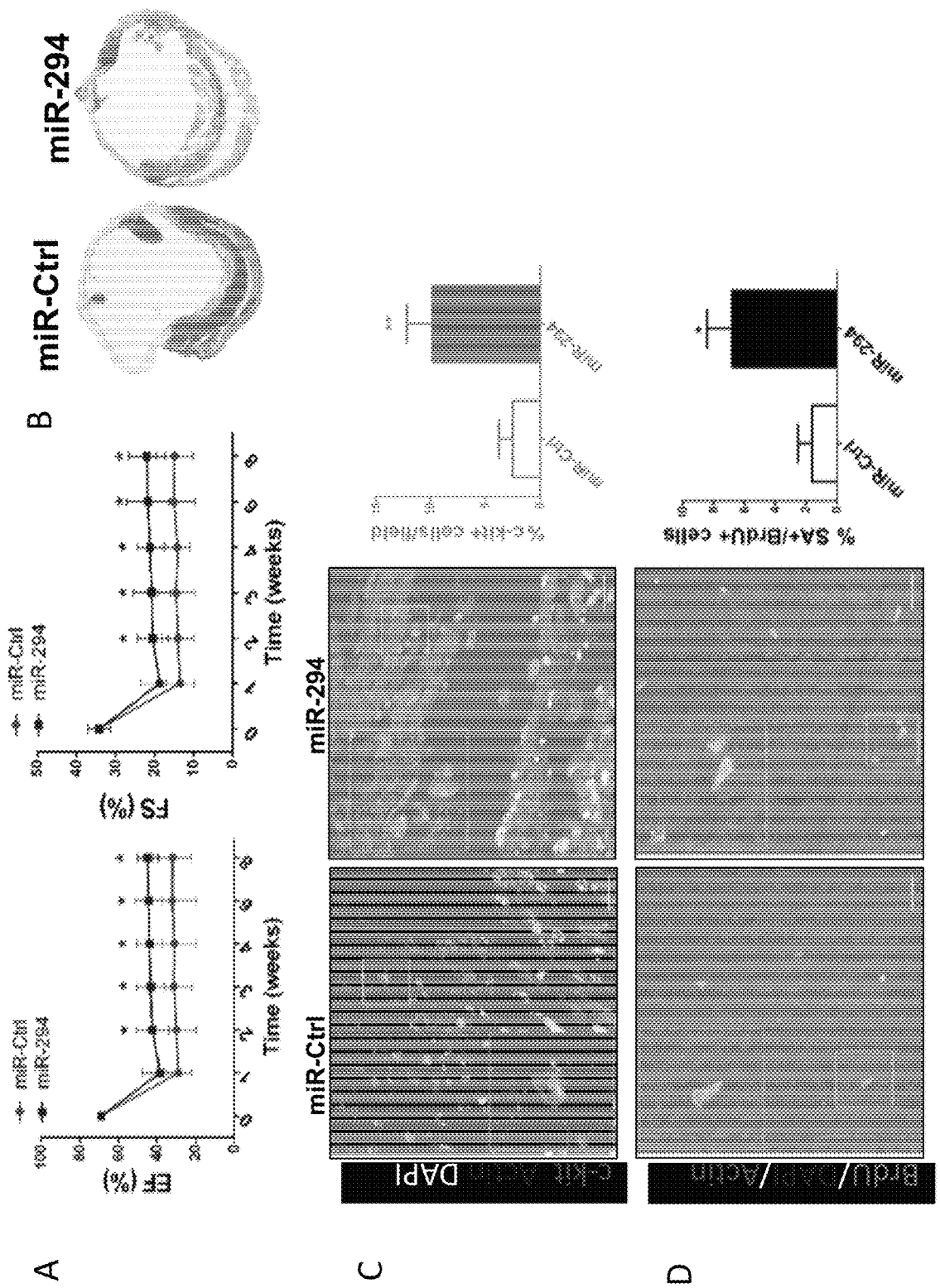
FIG. 21A through FIG. 21D, depicts the results of exemplary experiments demonstrating that administration of miR-294 in the heart after infarction augments cardiac function and cardiac proliferative response.

MiR-294 modulates cell cycle markers in neonatal rat cardiomyocytes including repression of Wee1 and upregulation of cell cycle markers (FIG. 18). Further, adult feline cardiomyocytes treated with miR-294 show increased cell cycle activity (FIG. 19). These results indicate that miR-294 promotes cell cycle re-entry in neonatal rat cardiomyocytes and adult cardiomyocytes. Proliferative effects of miR-294 are mediated by targeting of cell cycle markers in CPCs Administration of miR-294 in mice subjected to myocardial infarction demonstrated augmentation of cardiac function in mice receiving miR-294 8 weeks after injury. Increase myocyte proliferation along with increase in c-kit+ CPC numbers was observed in the heart after miR-294 treatment as analyzed by BrdU uptake, p-Histone 3 and Aurora B expression by immunostaining (FIG. 20). Concurrently, a decrease in infarct size along with decreased apoptosis was observed in the miR-294 hearts compared to the control (FIG. 21). These results indicate that the proliferative effects of miR-294 are mediated by targeting of cell cycle markers in CPCs. Further, ectopic expression of miR-294 recapitulates embryonic signaling and enhances cardiomyocyte ability to proliferate and reenter the cell cycle leading to augmented cardiac function in mice after myocardial infarction. Delivery of miR-294 in the heart augments cardiac function and increases proliferative response after myocardial infarction.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of increasing proliferation and metabolic activity of cardiomyocytes after myocardial infarction in a subject, the method comprising administering to a subject in need thereof an effective amount of a composition comprising an agent selected from the group consisting of a modified cardiomyocyte or CPC, and an exosome derived therefrom, wherein the cardiomyocyte or CPC has been modified with an activator of Lin28a, wherein the activator of Lin28a is.

2. The method of claim 1, wherein the CPC is autologous, allogeneic, syngeneic, or xenogeneic to the subject.

3. The method of claim 1, wherein the composition is administered to the subject by a route selected from the group consisting of local, topical, subcutaneous, intravenous, oral, intramuscular, and a combination thereof.

4. The method of claim 1, wherein the subject is a human.

* * * * *